US011426611B2

(12) United States Patent
Watson et al.

(10) Patent No.: US 11,426,611 B2
(45) Date of Patent: Aug. 30, 2022

(54) ULTRASOUND THERAPEUTIC AND SCANNING APPARATUS

(71) Applicant: ArcScan, Inc., Golden, CO (US)

(72) Inventors: John D. Watson, Evergreen, CO (US); Andrew K. Levien, Morrison, CO (US)

(73) Assignee: ArcScan, Inc., Golden, CO (US)

( * ) Notice: Subject to any disclaimer, the term of this patent is extended or adjusted under 35 U.S.C. 154(b) by 538 days.

(21) Appl. No.: 16/435,103

(22) Filed: Jun. 7, 2019

(65) Prior Publication Data
US 2019/0290939 A1  Sep. 26, 2019

Related U.S. Application Data

(63) Continuation-in-part of application No. 15/292,892, filed on Oct. 13, 2016, now Pat. No. 10,888,301.
(Continued)

(51) Int. Cl.
*A61B 8/00* (2006.01)
*A61N 7/02* (2006.01)
(Continued)

(52) U.S. Cl.
CPC ................ *A61N 7/02* (2013.01); *A61B 8/463* (2013.01); *A61B 90/37* (2016.02); *A61B 8/0833* (2013.01); *A61B 2090/378* (2016.02)

(58) Field of Classification Search
CPC combination set(s) only.
See application file for complete search history.

(56) References Cited

U.S. PATENT DOCUMENTS 3,371,660 A  3/1968 Benson
3,821,891 A  7/1974 Collins et al.
(Continued)

FOREIGN PATENT DOCUMENTS

CA  2295431  7/2001
CA  2299483  7/2001
(Continued)

OTHER PUBLICATIONS

"Campbell-Walsh Urology," Tenth Edition, W.B. Saunders, 2012, ISBN 978-1-4160-6911-9, abstract only, 2 pages.
(Continued)

*Primary Examiner* — Joel F Brutus
(74) *Attorney, Agent, or Firm* — Sheridan Ross P.C.

(57) ABSTRACT

The present disclosure is directed to a precision ultrasound scanner for imaging, for example, the prostate in a way that produces a superior image of the prostate while removing the iatrogenic risk and patient discomfort associated with other methods of providing an ultrasound image of the prostate. The present disclosure describes an apparatus and method for forming a high precision image of the prostate from outside the patient's body wherein the resolution in sufficient to image, for example, cancerous lesions on the surface of the prostate. To achieve such images, coded excitation, tissue harmonic imaging, advanced transducers operating in the 10 MHz to 40 MHz range is used to achieve a useable signal-to-noise reflection while being able to position the imaging transducer as close as possible to the prostate without risk or discomfort to the patient. The present disclosure further discloses an imaging transducer and an irradiating therapeutic transducer can be mounted such that they are movable between a plurality of positions. The irradiating transducer is, for example, about a 12 MHz transducer with a focal length of about 20 mm to about 40 mm that would produce a strong second harmonic at about 24 MHz that could be used for imaging. The imaging transducer has, for example, a focal length of about 10 mm to about 20 mm and typically operates in the range of about 25 MHz to about 40 MHz.

20 Claims, 12 Drawing Sheets

Related U.S. Application Data

(60) Provisional application No. 62/240,636, filed on Oct. 13, 2015.

(51) Int. Cl.
*A61B 90/00* (2016.01)
*A61B 8/08* (2006.01)

(56) References Cited

U.S. PATENT DOCUMENTS

| | | | |
|---|---|---|---|
| 3,997,793 A | 12/1976 | Rogers et al. | |
| 4,092,867 A | 6/1978 | Matzuk | |
| 4,114,214 A | 9/1978 | VonHeck | |
| 4,154,114 A | 5/1979 | Katz | |
| 4,183,249 A | 1/1980 | Anderson | |
| 4,206,763 A | 6/1980 | Pedersen | |
| 4,227,780 A | 10/1980 | Ohta et al. | |
| 4,233,988 A | 11/1980 | Dick | |
| 4,245,250 A | 1/1981 | Tiemann | |
| 4,282,755 A | 8/1981 | Gardineer et al. | |
| 4,347,213 A | 8/1982 | Rogers | |
| 4,484,569 A | 11/1984 | Driller et al. | |
| 4,493,877 A | 1/1985 | Burnett | |
| 4,545,385 A | 10/1985 | Pirschel | |
| 4,550,607 A | 11/1985 | Maslak et al. | |
| 4,564,018 A | 1/1986 | Hutchison et al. | |
| 4,807,634 A | 2/1989 | Enjoji et al. | |
| 4,815,047 A | 3/1989 | Hart | |
| 4,817,432 A | 4/1989 | Wallace et al. | |
| 4,823,801 A | 4/1989 | Sakane | |
| 4,858,124 A | 8/1989 | Lizzi et al. | |
| 4,858,613 A | 8/1989 | Fry et al. | |
| 4,930,512 A | 6/1990 | Henriksen et al. | |
| 4,932,414 A | 6/1990 | Coleman et al. | |
| 5,029,587 A | 7/1991 | Baba et al. | |
| 5,079,786 A | 1/1992 | Rojas | |
| 5,103,517 A | 4/1992 | Krouskop | |
| 5,116,114 A | 5/1992 | Nakamura et al. | |
| 5,152,746 A | 10/1992 | Atkinson et al. | |
| 5,293,871 A | 3/1994 | Reinstein et al. | |
| 5,331,962 A | 7/1994 | Cdeman et al. | |
| 5,369,454 A | 11/1994 | Reinstein et al. | |
| 5,387,180 A | 2/1995 | Lehmer | |
| 5,460,179 A | 10/1995 | Okunuki et al. | |
| 5,474,070 A | 12/1995 | Ophir et al. | |
| 5,487,388 A | 1/1996 | Rello et al. | |
| 5,517,991 A | 5/1996 | Herrmann et al. | |
| 5,551,432 A | 9/1996 | Iezzi | |
| 5,556,169 A | 9/1996 | Parrish et al. | |
| 5,614,099 A | 3/1997 | Hirose et al. | |
| 5,626,150 A | 5/1997 | Johnson et al. | |
| 5,626,594 A | 5/1997 | Smith | |
| 5,647,367 A | 7/1997 | Lum et al. | |
| 5,671,739 A | 9/1997 | Darrow et al. | |
| 5,776,068 A | 7/1998 | Silverman et al. | |
| 5,826,583 A | 10/1998 | Wood | |
| 5,832,550 A | 11/1998 | Hauger et al. | |
| 5,855,207 A | 1/1999 | Moenning et al. | |
| 5,906,205 A | 5/1999 | Hiebert | |
| 5,966,763 A | 10/1999 | Thomas | |
| 5,971,006 A | 10/1999 | Seigerschmidt | |
| 6,053,613 A | 4/2000 | Wei et al. | |
| 6,145,143 A | 11/2000 | Hicks et al. | |
| 6,154,204 A | 11/2000 | Thompson et al. | |
| 6,198,956 B1 | 3/2001 | Dunne | |
| 6,315,727 B1 | 11/2001 | Coleman et al. | |
| 6,318,372 B1 | 11/2001 | Hiebert | |
| 6,334,227 B1 | 1/2002 | Larger | |
| 6,374,439 B2 | 4/2002 | Helmbrock et al. | |
| 6,451,008 B1 | 9/2002 | Frey et al. | |
| 6,460,207 B1 | 10/2002 | Papay et al. | |
| 6,487,447 B1 | 11/2002 | Weimann et al. | |
| 6,491,637 B2 | 12/2002 | Foster et al. | |
| 6,574,813 B2 | 6/2003 | Bolden et al. | |
| 6,629,929 B1 | 10/2003 | Jago et al. | |
| 6,684,433 B2 | 2/2004 | Giori et al. | |
| 6,780,153 B2 | 8/2004 | Angelsen et al. | |
| 6,837,855 B1 | 1/2005 | Puech | |
| 6,868,569 B2 | 3/2005 | VanSteenburg | |
| 6,887,203 B2 | 5/2005 | Phillips et al. | |
| 6,923,767 B2 | 8/2005 | Saied et al. | |
| 6,981,417 B1 | 1/2006 | Oravecz | |
| 7,048,690 B2 | 5/2006 | Coleman et al. | |
| 7,168,116 B2 | 1/2007 | Reger et al. | |
| 7,237,898 B1 | 7/2007 | Hohla | |
| 7,356,905 B2 | 4/2008 | Ketterling et al. | |
| 7,451,507 B2 | 11/2008 | Brinkerhoff et al. | |
| 7,454,024 B2 | 11/2008 | Ketterling et al. | |
| 7,474,041 B2 | 1/2009 | Ketterling et al. | |
| 7,480,058 B2 | 1/2009 | Zhao et al. | |
| 7,611,507 B2 | 11/2009 | Raksi et al. | |
| 7,708,342 B2 | 5/2010 | Leach | |
| 7,920,909 B2 | 4/2011 | Lyon et al. | |
| 8,064,989 B2 | 11/2011 | Brown et al. | |
| 8,068,647 B2 | 11/2011 | Lin | |
| 8,115,935 B2 | 2/2012 | Everett et al. | |
| 8,317,709 B2 | 11/2012 | Ellers et al. | |
| 8,475,384 B2 | 7/2013 | Hart et al. | |
| 8,496,588 B2 | 7/2013 | Eilers et al. | |
| 8,510,883 B2 | 8/2013 | Eilers et al. | |
| 8,732,878 B2 | 5/2014 | Eilers et al. | |
| 8,758,252 B2 | 6/2014 | Eilers et al. | |
| 8,824,743 B2 | 9/2014 | Daigle | |
| 9,039,623 B2 | 5/2015 | Eilers et al. | |
| 9,149,254 B2 | 10/2015 | Watson | |
| 9,320,427 B2 | 4/2016 | Levien et al. | |
| 9,597,059 B2 | 3/2017 | Watson et al. | |
| 10,265,049 B2 | 4/2019 | Levien et al. | |
| 2001/0020200 A1 | 9/2001 | Das et al. | |
| 2002/0085173 A1 | 7/2002 | Schipper et al. | |
| 2002/0143252 A1 | 10/2002 | Dunne et al. | |
| 2003/0142269 A1 | 7/2003 | Cumming | |
| 2004/0200754 A1 | 10/2004 | Hagemeier | |
| 2004/0220478 A1 | 11/2004 | Wallace et al. | |
| 2005/0008527 A1 | 1/2005 | Bayer et al. | |
| 2005/0067494 A1 | 3/2005 | Ito et al. | |
| 2005/0120479 A1 | 6/2005 | Habashi et al. | |
| 2005/0143638 A1 | 6/2005 | Johnson et al. | |
| 2006/0029525 A1 | 2/2006 | Laugharn, Jr. et al. | |
| 2006/0058717 A1 | 3/2006 | Hui et al. | |
| 2006/0074287 A1 | 4/2006 | Neumann et al. | |
| 2006/0106313 A1 | 5/2006 | Hobson | |
| 2006/0241533 A1 | 10/2006 | Geller | |
| 2006/0288487 A1 | 12/2006 | Roleder et al. | |
| 2007/0051362 A1 | 3/2007 | Sullivan et al. | |
| 2007/0083995 A1 | 4/2007 | Purdy et al. | |
| 2007/0239020 A1 | 10/2007 | Iinuma et al. | |
| 2007/0239030 A1 | 10/2007 | Prager et al. | |
| 2007/0276233 A1 | 11/2007 | Besson et al. | |
| 2008/0097214 A1 | 4/2008 | Meyers et al. | |
| 2008/0146939 A1 | 6/2008 | McMorrow et al. | |
| 2008/0161696 A1 | 7/2008 | Schmitt et al. | |
| 2009/0088623 A1 | 4/2009 | Vortman et al. | |
| 2009/0234369 A1 | 9/2009 | Bax et al. | |
| 2009/0318758 A1 | 12/2009 | Farr et al. | |
| 2010/0004538 A1* | 1/2010 | Eilers | A61B 8/4461 600/444 |
| 2010/0031448 A1 | 2/2010 | Hikema | |
| 2010/0217125 A1 | 8/2010 | Kadokura et al. | |
| 2010/0229306 A1 | 9/2010 | Reeder et al. | |
| 2010/0249562 A1 | 9/2010 | Zhang | |
| 2010/0321697 A1 | 12/2010 | Zheng et al. | |
| 2011/0172511 A1 | 7/2011 | Peterson et al. | |
| 2012/0053459 A1 | 3/2012 | Eilers et al. | |
| 2012/0089021 A1* | 4/2012 | Peyman | A61B 8/4477 600/439 |
| 2012/0209118 A1 | 8/2012 | Warnking | |
| 2012/0320368 A1 | 12/2012 | Jiao | |
| 2013/0072755 A1 | 3/2013 | Papania et al. | |
| 2013/0085370 A1 | 4/2013 | Friedman | |
| 2013/0237826 A1 | 9/2013 | Levien | |
| 2014/0155747 A1* | 6/2014 | Bennett | A61N 7/02 600/439 |
| 2014/0249422 A1 | 9/2014 | Eilers et al. | |

(56) References Cited

U.S. PATENT DOCUMENTS

| | | |
|---|---|---|
| 2014/0268037 A1 | 9/2014 | Siminou |
| 2014/0371589 A1 | 12/2014 | Nakabayashi |
| 2015/0031998 A1 | 1/2015 | Kyono et al. |
| 2015/0238166 A1 | 8/2015 | Heath et al. |
| 2015/0265243 A1 | 9/2015 | Kelly |
| 2016/0270762 A1 | 9/2016 | Eilers et al. |
| 2017/0119345 A1 | 5/2017 | Levien et al. |

FOREIGN PATENT DOCUMENTS

| | | |
|---|---|---|
| CA | 2395203 | 7/2001 |
| CA | 2409234 | 4/2004 |
| JP | 2006-149001 | 6/2006 |
| WO | WO 2013/103167 | 7/2013 |

OTHER PUBLICATIONS

"Information for Manufacturers Seeking Marketing Clearance of Diagnostic Ultrasound Systems and Transducers", 2008, Center for Devices and Radiological Health, 68 pages.

Angelson et al. "Which transducer array is best?" European Journal of Ultrasound, 1995, vol. 2., pp. 151-164.

Binder, "SL-OCT and Ultrasound Support the Need for New Phakic IOL Sizing Strategies," Euro Times, Mar. 2007, p. 11.

Coleman et al., "Ultrasonography of the Eye and Orbit," Second Edition, published by Lippincott Williams & Wilkins, 2006, 205 pages, uploaded in 4 parts.

Izatt et al., "Theory of Optical Coherence Tomography," Chap. 2 of "Optical Coherence Tomography Technology and Applications," Drexler and Fujimoto eds, ISBN:978-3-540-77549-2, 2008, 27 pages.

Ketterling, "Design and Fabrication of a 40-MHz Annular Array Transducer," IEEE Transactions on Ultrasonics, Ferroelectrics, and Frequency Control, Apr. 2005, vol. 52, No. 4, pp. 672-681.

Ketterling, "Operational Verification of a 40-MHz Annular Array Transducer," IEEE Transactions on Ultrasonics, Ferroelectrics, and Frequency Control, Mar. 2006, vol. 53, No. 3, pp. 623-630.

Kim et al., "20 MHz/40 MHz Dual Element Transducers for High Frequency Harmonic Imaging," IEEE Transactions on Ultrasonics, Ferroelectrics and Frequency Control, 2008, vol. 55(12). pp, 2683-2691, 25 pages.

Mamou, "Chirp-Coded Excitation imaging With a High-Frequency Ultrasound Annular Array," IEEE Transactions on Ultrasonics, Ferroelectrics, and Frequency Control, Feb. 2008, vol. 55, No. 2, pp. 508-513.

Misaridis et al., "Use of Modulated Excitation Signals in Medical Ultrasound. Part I: Basic Concepts and Expected Benefits," IEEE Transactions on Ultrasonics, Ferroelectrics, and Frequency Control, 2005, vol. 52(2), pp. 177-191.

Pinero et al., "Equivalence, Differences Identified in Biometric Analysis," Cataract & Refractive Surgery Today, Mar. 2008, vol. 3, No. 12, 4 pages.

Reinstein et al., "Repeatability of Layered Corneal Pachymetry With the Artemis Very High Frequency Digital Ultrasound Arc-Scanner," J. Refractive Surg., vol. 26(9), 2009, original article, 14 pages.

Reinstein, "Subsurface Screening for Keratoconus—Accurate Measurements of the Epithelial and Stromal Layers Aid in Diagnosis," Cataract and Refractive Surgery Today, May 2007, pp. 88-89.

Roholt, "Sizing the Visian ICL" Cataract and Refractive Surgery Today, May 2007, p. 50.

Sanchez et al., "A Novel Coded Excitation Scheme to Improve Spatial and Contrast Resolution of Quantitative Ultrasound Imaging," IEEE Transactions on Ultrasonics, Ferroelectrics, and Frequency Control, 2009, vol. 56(10), pp. 2111-2123, abstract only, 1 page.

Silverman et al., "High-Frequency Ultrasonic Imaging of the Anterior Segment Using an Annular Array Transducter," Ophthalmology, 2007, vol. 114(4), pp. 816-822, 15 pages.

Silverman et al., "Improved System for Sonographic Imaging and Biometry of the Cornea," J. Ultrasound Med., 1997, vol. 16, pp. 117-124.

Song et al., "Coded excitation for ultrasound tissue harmonic imaging," Ultrasonics, received in revised form 18, Dec. 2009, retrieved from journal homepage: www.elsevier.com/locate/ultras, pp. 1-7.

International Search Report and Written Opinion for International (PCT) Patent Application No. PCT/US2016/056863, dated Feb. 24, 2017 13 pages.

Official Action for U.S. Appl. No. 15/292,892, dated Apr. 19, 2019, 24 pages.

Official Action for U.S. Appl. No. 15/292,592, dated Jan. 23, 2020, 24 pages.

Official Action for U.S. Appl. No. 15/292,892, dated Aug. 21, 2020, 16 pages.

Notice of Allowance for U.S. Appl. No. 15/292,892, dated Oct. 30, 2020, 9 pages.

U.S. Appl. No. 12/638,661, filed Dec. 15, 2009, now issued as U.S. Pat. No. 8,317,709.

U.S. Appl. No. 12/418,392, filed Apr. 3, 2009, now issued as U.S. Pat. No. 8,496,588.

U.S. Appl. No. 12/754,444, filed Apr. 5, 2010, now issued as U.S. Pat. No. 8,510,883.

U.S. Appl. No. 13/969,778, filed Aug. 19, 2013, now issued as U.S. Pat. No. 8,732,878.

U.S. Appl. No. 12/347,674, filed Dec. 31, 2008, now issued as U.S. Pat. No. 8,758,252.

U.S. Appl. No. 12/475,322, filed May 29, 2009, now issued as U.S. Pat. No. 9,039,623.

U.S. Appl. No. 13/684,699, filed Nov. 26, 2012, now issued as U.S. Pat. No. 9,149,254.

U.S. Appl. No. 13/937,948, filed Jul. 9, 2013, now issued as U.S. Pat. No. 9,320,427.

U.S. Appl. No. 13/894,741, filed May 15, 2013, now issued as U.S. Pat. No. 9,597,059.

U.S. Appl. No. 15/048,706, filed Feb. 19, 2016, now issued as U.S. Pat. No. 10,265,049.

U.S. Appl. No. 13/796,931, filed Mar. 12, 2013, now issued as U.S. Pub. No. 2013/0237826.

U.S. Appl. No. 14/278,960, filed May 15, 2014, now issued as U.S. Pub. No. 2014/0249422.

U.S. Appl. No. 14/630,101, filed Feb. 24, 2015, now issued as U.S. Pub. No. 2015/0238166.

U.S. Appl. No. 15/081,549, filed Mar. 25, 2016, now issued as U.S. Pub. No. 2016/0270762.

U.S. Appl. No. 15/292,892, filed Oct. 13, 2016, now issued as U.S. Pub. No. 2017/0119345.

\* cited by examiner

Top View

Side View

End View

Top View

Side View

End View

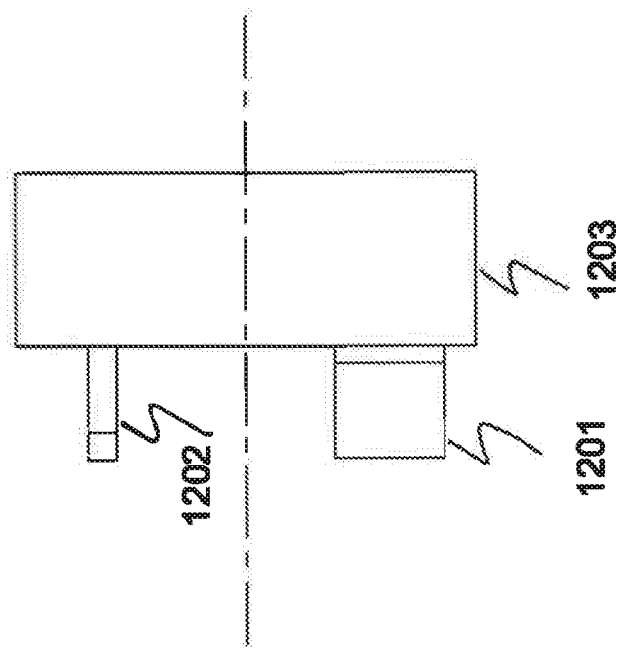
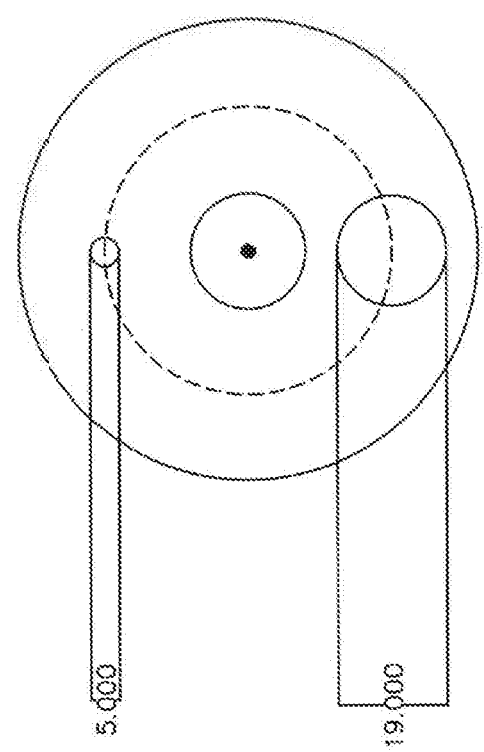
Fig. 12b
Fig. 12a

ULTRASOUND THERAPEUTIC AND SCANNING APPARATUS

CROSS-REFERENCE TO RELATED APPLICATIONS

This application is a continuation-in-part of U.S. patent application Ser. No. 15/292,892 entitled "Ultrasound Scanning Apparatus" filed Oct. 13, 2016, which claims the benefit of U.S. provisional patent application Ser. No. 62/240,636 entitled "Ultrasound Scanning Apparatus" filed Oct. 13, 2015. The entireties of the aforementioned applications are incorporated herein by reference.

FIELD OF INVENTION

The present disclosure relates to the use of ultrasound as a non-invasive means of both irradiating and imaging biological materials such the heart, liver, spleen and prostate and in particular directed to an apparatus for a low iatrogenic risk, easily implemented method for precision ultrasound irradiating and imaging of the prostate gland.

BACKGROUND

Ultrasound imaging of body parts, including the eye has been pursued for a number of years. Ultrasound Bio Microscopy (UBMs) are hand-held devices that have been available for years but are not suitable for precision measurements. An arc scanner has been developed and tested for ultrasound scanning of the eye under the names of Artemis 1, Artemis 2, Artemis 3 and the ArcScan Insight 100. These devices have given improved ultrasound scans of the eye by utilizing a precision registration system and by using an eye seal to provide a continuous water (or water equivalent) path from the transducer to the eye (the eye has acoustic properties similar to water).

The ArcScan Insight 100 can make B-scans of an eye with a resolution of about 30 microns and a repeatability of about 2 to 5 microns using a single element transducer operating at a center frequency of about 40 MHz. Other workers in the field have used lower frequency transducers in the 5 to 10 MHz range to image the retina of an eye (the retina is on the order of 25 mm from the anterior surface of the cornea). Others have participated in work using annular array transducers and linear transducer arrays as well as coded excitation techniques for imaging the eye and other body parts with ultrasound.

Many of the ArcScan Insight 100 hardware innovations (such fluid bearings and arc scanning with variable radii of curvature) and many of the well-known ultrasound image enhancement techniques (such as annular array transducers, coded excitation, advanced data processing) can be combined to provide a precision ultrasound scanner for other body parts.

The prostate gland can be imaged by X-rays, MRI (magnetic resonance imaging) or ultrasound. Imaging by ultrasound is non-ionizing and less risky than imaging by X-rays and is far more convenient than imaging by MRI.

Ultrasound imaging can be accomplished by a hand-held sector scanner device or by a trans-rectal ultrasound probe. The hand-held sector scanner can make a qualitative image of the prostate by imaging through the abdominal wall but resolution is typically poor. This is a low iatrogenic risk procedure and easily applied imaging technique but the image quality is too poor to make informed decisions, for example about cancer cell development. The trans-rectal ultrasound probe can make a better image than a hand-held sector scanner because the ultrasound transducer can be positioned within 10 or 20 millimeters of the prostate gland on the other side of the rectal wall from the prostate. The image is difficult to co-register successive B-scans and so is not quite precise and accurate enough to make informed decisions about, for example, cancer cell development. In addition, a trans-rectal ultrasound probe causes some discomfort to the patient and has moderate iatrogenic risk. The procedure can lead to infections if the endoscope is improperly sterilized or more severe problems if the probe pierces the rectal wall, as occasionally happens.

High-intensity focused ultrasound (HIFU) is a non-invasive therapeutic technique that uses non-ionizing ultrasonic waves to heat tissue. HIFU can be used to increase the flow of blood or to destroy tissue, such as tumors, through a number of mechanisms. The technology is similar to ultrasonic imaging, although practiced at lower frequencies and higher acoustic power. Acoustic lenses may be used to achieve the necessary intensity at the target tissue without damaging the surrounding tissue.

A focused ultrasound system is used to treat essential tremor, neuropathic pain and Parkinsonian tremor. The focused ultrasound approach enables treatment of the brain without an incision or radiation. Treatment for symptomatic uterine fibroids became the first approved application of HIFU by the US Food and Drug Administration (FDA) in October 2004. Studies have shown that HIFU is safe and effective, and that patients have sustained symptomatic relief is sustained for at least two years without the risk of complications involved in surgery or other more invasive approaches.

HIFU has been successfully applied in treatment of cancer to destroy solid tumors of the bone, brain, breast, liver, pancreas, rectum, kidney, testes, prostate.

There remains a need for a low iatrogenic risk, easily implemented method of ultrasound irradiation and imaging for the prostate that produces a superior image that can be used as a screening tool and treatment procedure for diseases of the prostate.

SUMMARY

These and other needs are addressed by the present disclosure. The various embodiments and configurations of the present disclosure are directed generally to ultrasound imaging of biological materials such the heart, liver, spleen and prostate and in particular directed to a method and apparatus for a precision ultrasound scanning and treatment of the prostate gland. The present disclosure describes two modes of applying ultrasound technology for both irradiating and imaging biological materials such the heart, liver, spleen and prostate and in particular directed to an apparatus for use in a non-invasive, low iatrogenic risk method for precision ultrasound irradiating and scanning of the prostate and other organs.

In one mode, a high-intensity focused ultrasound source is used along with a higher frequency diagnostic ultrasound source to alternately provide the required irradiating and then imaging capability through the perineum.

A system is disclosed for treating and imaging a body part of a patient, comprising a housing defining an enclosed volume, wherein the enclosed volume is at least partially filled with a fluid. The system further includes a transducer holder positioned in the fluid in the enclosed volume of the housing, wherein the transducer holder is movable between or among a plurality of positions. The system further includes a first ultrasound transducer positioned on the transducer holder, wherein the first ultrasound transducer emits a first ultrasound wave in a first frequency range; a second ultrasound transducer positioned on the transducer holder, wherein the second ultrasound transducer emits a second ultrasound wave in a second frequency range. The first and second frequency ranges are distinct, and the transducer holder moves such that one of the first or second ultrasound transducers is in an emission position of the plurality of positions to emit one of the first or second ultrasound waves, respectively, into a body part of a patient.

A method is disclosed for treating and imaging a body part of a patient, comprising providing a housing with an acoustically-transparent window on a surface of the housing, wherein the housing is at least partially filled with a fluid; and providing a first ultrasound transducer and a second ultrasound transducer in the fluid in the housing, wherein the first ultrasound transducer emits a first ultrasound wave in a first frequency range, the second ultrasound transducer emits a second ultrasound wave in a second frequency range, and the first and second frequency ranges are distinct. The method further includes positioning a patient on the housing with a body part positioned over the acoustically-transparent window; emitting the first ultrasound wave from the first ultrasound transducer to image the body part of the patient; emitting the second ultrasound wave from the second ultrasound transducer to treat the body part of the patient; and emitting the first ultrasound wave from the first ultrasound transducer to re-image the body part of the patient.

In a second mode, a high-intensity focused ultrasound source is used alone and the detection of higher frequency harmonics by methods generally known as tissue harmonic imaging are used to overcome high frequency ultrasound attenuation and deliver the imaging resolution required for screening and diagnosis.

This first mode of operation can be extended to include coded excitation and tissue harmonic imaging techniques to produce images at different frequencies and with two different focal length transducers. This combination, for example, could be used to irradiate the target organ with non ionizing ultrasound while taking images of the target organ at 12 MHz, 24 MHz, and 40 MHz.

A system is disclosed for treating and imaging a body part of a patient, comprising a housing defining an enclosed volume, wherein the enclosed volume is at least partially filled with a fluid; an acoustically-transparent window on a surface of the housing; a transducer holder positioned in the fluid in the enclosed volume of the housing; and a first ultrasound transducer positioned on the transducer holder, wherein the first ultrasound transducer emits a first ultrasound wave at a first frequency in a first frequency range through the acoustically-transparent window and into a body part of a patient, and the first ultrasound transducer receives a harmonic wave at a harmonic frequency that is approximately twice the frequency of the first frequency from the body part of a patient after through the acoustically-transparent window.

In the present disclosure, known techniques can be combined in some embodiments to achieve high resolution and tissue depths of 60 millimeters or more. These include the use of annular arrays of two or more independent transducer elements; coded excitation of transmitted ultrasound pulses; and detection of higher frequency harmonics in methods generally known as tissue harmonic imaging.

An innovation of the present disclosure is the use of different types of seating apparatuses that allow the use of a precision arc scanning instrument to be used while minimizing or eliminating iatrogenic risk and patient discomfort. This approach provides for imaging and treatment of the prostate gland from outside the body through the perineum so that the ultrasound probe or probes can get close to the prostate and avoid bony structures that would severely attenuate ultrasound energy.

The elements of a precision ultrasound scanning apparatus for imaging a prostate can include:

1. A scanning instrument container formed by a saddle (on which the patient sits) and an instrument body under the saddle. The instrument body contains the scanning apparatus and can be filled with a liquid such as distilled water. Alternately, the scanning instrument container can be formed by a bowl (on which the patient sits) and an instrument body within the bowl. The instrument body contains the scanning apparatus and wherein the instrument body can be filled with a liquid such as distilled water.
2. The scanning instrument container formed by a saddle can house the scanning instrument and can also comprise stirrups for the patient's feet, and handle bars. The stirrups and handle bars can allow the patient to lean forward to assume an optimal position for scanning.
3. A scanning apparatus contained within the scanning instrument container that can comprise an x-y-z-beta positioning mechanism; a scan head that can comprise an arcuate guide track and/or a linear guide track; a transducer probe carriage that moves along one of the guide tracks; a transducer which can be a single element needle probe, an annular array probe or a linear a transducer array. The scanning apparatus can include a video camera that can provide an optical image of the outside of the body part being scanned by the ultrasound probe. The positioning mechanism may able to tilt the scan head. Tilting means changing the tilt angle of the positioner mechanism and scan head by rotating about the x-axis in the y-z plane. The arcuate guide track is aligned with the x-axis such that the transducer carriage moves back and forth in an arc aligned with the x-axis. A linear guide track would also be aligned with the x-axis such that the transducer carriage moves back and forth parallel to the x-axis.
4. A computer, comprising input and/or output devices that controls the scanning apparatus (controls the positioning mechanism, the scan head motion, the transmitting and receiving of the ultrasound probe and the manipulation of A-scans to form a B-scan of the prostate gland).
5. A detachable window connected to and embedded in the saddle or bowl of the scanning instrument container. The window is made from a material that can transmit optical and acoustic energy. The window may be round, elliptical or square with rounded corners such that the window can allow the scanner to scan the selected body part of the patient.
6. A disposable and deformable container of clear gel that can conform to the detachable window in the saddle and to the body part being scanned by the ultrasound probe. For example, a disposable bag of gel can be placed over the window. The patient sits on the bag so that the gel is in contact with the window and with the patient's body. Alternately, the disposable and deformable container could, for example, be a pair of shorts with the disposable and deformable container of clear gel sewn into the crotch area of the shorts.

The configuration of the scanning instrument container formed by a saddle or bowl on which the patient sits can allow the scan to be conducted upwards through the patient's perineum thereby providing a short transmission/receiving path to the prostate while remaining a non-invasive procedure that minimizes patient discomfort and risk of infection. This configuration, as well as other configurations discussed, are designed to 1) provide a continuous fluid path of substantially similar acoustic transmission properties from the ultrasound transducer to the body part being scanned and 2) minimize the distance between the ultrasound transducer to the body part being scanned.

In the example of the prostate gland, the frequency characteristic of the ultrasound probe and the peak power of the transducer emissions are commonly selected so that an image of the prostate can be formed when the prostate is about 50 to 130 millimeters from the face of the transducer element. The center frequency of the probe may be in the range of about 10 MHz to about 40 MHz to provide the required image resolution.

The peak power output of the ultrasound probe will be within the limits established by the FDA or other regulatory body. For example, a spatial-peak pulse-average intensity of 94 mW/cm$^2$ and a spatial-peak temporal-average intensity of 190 W/cm2 would be allowable under 2008 FDA guidelines (Publication Reference 4) for the prostate gland. This compares to a spatial-peak pulse-average intensity of 17 mW/cm$^2$ and a spatial-peak temporal-average intensity of 28 W/cm2 allowable under current FDA guidelines for ophthalmic imaging. This represents a six-fold increase in transducer power over allowable ophthalmic imaging transducer power (a scan depth of about 6 to 7.5 mm for anterior segment scanning of the human eye and a scan depth of about 25 mm for retinal scanning of the human eye).

It is noted that attenuation of signal strength in body tissue is typically about 0.5 dB per cm per MHz.

The present disclosure can utilize annular array transducers to increase the depth of tissue that can be scanned since annular array transducers can transmit at its characteristic frequency and receive at the characteristic frequency or at twice the characteristic frequency.

The present disclosure can also utilize coded excitation techniques such as chirp-coded excitation or Golay code excitation, for example, and over-sampling techniques to increase signal-to-noise ratio thereby allowing deeper imaging capability. As in the ultrasound device described herein for scanning the eye, the noise floor of the data acquisition system is typically the noise figure associated with the amplifier input to the A/D device.

The method of the present disclosure using the above described saddle or bowl apparatus can include the following steps:
1. The scanning instrument container is filled with distilled water
2. The disposable and deformable container of clear gel is placed on the saddle and the patient sits on the container of clear gel in preparation for scanning. Alternately, the patient puts on the disposable shorts and sits on the saddle or bowl.
3. When the probe is centered on the arcuate guide track, the video camera is used to position the ultrasound probe on the area of interest of the patient. In this operation, the positioner assembly moves the scan head into position for scanning.
4. Scans are then made at different depths of focus and at different meridians by:
$ aligning the arcuate guide track by rotating the arcuate guide assembly about its beta axis
$ translating the scan head by small amounts
$ tilting the scan head assembly by small amounts The above general procedure can be similar to that used for ultrasound scanning of an eye using an arc scanning device. The above scanning modes are discussed in further detail in FIGS. 9A-9F.

The following definitions are used herein:

The phrases at least one, one or more, and and/or are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

Acoustic impedance means the product of sound speed times density, ρc, where ρ is the density (~993 kg/cu meter for water at 37 C) and c is the sound speed (1,520 meters per second at 37 C). Thus acoustic impedance of water at 37 C is about 1.509×10$^6$ kg/(sq meter-sec) or 1.509 Mrayls.

An acoustically reflective surface or interface is a surface or interface that has sufficient acoustic impedance difference across the interface to cause a measurable reflected acoustic signal. A specular surface is typically a very strong acoustically reflective surface.

Anterior means situated at the front part of a structure; anterior is the opposite of posterior.

An A-scan is a representation of a rectified, filtered reflected acoustic signal as a function of time, received by an ultrasonic transducer from acoustic pulses originally emitted by the ultrasonic transducer from a known fixed position relative to a body component.

Accuracy as used herein means substantially free from measurement error.

Aligning means positioning the acoustic transducer accurately and reproducibly in all three dimensions of space with respect to a feature of the body component of interest (such as the heart, liver, spleen and prostate, etcetera).

An arc scanner, as used herein, is an ultrasound eye scanning device where the ultrasound transducer moves back and forth along an arcuate guide track wherein the focal point of the ultrasound transducer is typically placed somewhere within the eye near the region of interest (i.e. the corneas, the lens etcetera). The scanner may also include a linear guide track which can move the arcuate guide track laterally such that the effective radius of curvature of the arcuate track is either increased or decreased. The scanner utilizes a transducer that both sends and receives pulses as it moves along 1) an arcuate guide track, which guide track has a center of curvature whose position can be moved to scan different curved surfaces; 2) a linear guide track; and 3) a combination of linear and arcuate guide tracks which can create a range of centers of curvature whose position can be moved to scan different curved surfaces.

Automatic refers to any process or operation done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material."

Auto-centering means automatically, typically under computer control, causing centration of the arc scanning transducer with the body component of interest.

Body habitus is somewhat redundant, since habitus by itself means "physique or body build.". Body size and habitus describe the physical characteristics of an individual and include such considerations as physique, general bearing, and body build.

A B-scan is a processed representation of A-scan data by either or both of converting it from a time to a distance using acoustic velocities and by using grayscales, which correspond to A-scan amplitudes, to highlight the features along the A-scan time history trace (the latter also referred to as an A-scan vector).

Centration means substantially aligning the center of curvature of the arc scanning transducer in all three dimensions of space with the center of curvature of the eye component of interest (such as the cornea, pupil, lens, retina, etcetera) such that rays from the transducer pass through both centers of curvature. A special case is when both centers of curvature are coincident.

Coded excitations are engineered excitation pulses that are capable of increasing the effective penetration depth of a transmitted signal in echo location imaging systems such as radar, sonar and ultrasound, by improving the signal-to-noise ratio (SNR).

Chirping is a coded excitation that can be thought of as a complex exponential sequence with linearly increasing frequency. A linear chirp is a coded signal that linearly spans a frequency bandwidth $B=f_2-f_1$, where $f_1$ and $f_2$ are the starting and ending frequencies, respectively. If the chirp sweeps from $f_1$ to $f_2$ over a time, then the chirp-coded excitation is described by: $s(t)=\omega(t) \cos(2\pi f_1 t+\pi b t^2)$.

Fiducial means a reference, marker or datum in the field of view of an imaging device.

Fixation means having the patient focus an eye on an optical target such that the eye's optical axis is in a known spatial relationship with the optical target. In fixation, the light source is axially aligned in the arc plane with the light source in the center of the arc so as to obtain maximum signal strength such that moving away from the center of the arc in either direction results in signal strength diminishing equally in either direction away from the center.

A guide is an apparatus for directing the motion of another apparatus.

Hand-held ultrasonic scanner See Ultrasound Bio Microscopy (UBM).

HIFU Means High-Intensity Focused Ultrasound.

The home position of the imaging ultrasound transducer is its position during the registration process.

An iatrogenic risk is a risk due to the activity of a physician or surgeon or by medical treatment or diagnostic procedures. For example, an iatrogenic illness is an illness that is caused by a medication or physician.

An imaging ultrasound transducer is the device that is responsible for creating the outgoing ultrasound pulse and detecting the reflected ultrasound signal that is used for creating the A-Scans and B-Scans.

As used herein, a meridian is a 2-dimensional plane section through the approximate center of a 3-dimensional eye and its angle is commonly expressed relative to a horizon defined by the nasal canthus and temporal canthus of the eye.

A medical procedure is defined as non-invasive when no break in the skin is created and there is no contact with the mucosa, or skin break, or internal body cavity beyond a natural or artificial body orifice. Non-invasive procedures include specialized forms of surgery, such as radio surgery. extra corporeal shock wave lithotripsy (using an acoustic pulse for treatment of stones in the kidney, gallbladder or liver for example), The perineum is the pelvic floor and associated structures occupying the pelvic outlet, bounded anteriorly by the pubic symphysis, laterally by the ischial tuberosities, and posteriorly by the coccyx. The region between the scrotum and the anus in males, Positioner means the mechanism that positions a scan head relative to a selected part of an eye. In the present disclosure, the positioner can move back and forth along the x, y or z axes and rotate in the β direction about the z-axis. Normally the positioner does not move during a scan, only the scan head moves. In certain operations, such as measuring the thickness of a region, the positioner may move during a scan.

Position tracking sensors are a set of position sensors whose sole purpose is to monitor the movement of the eye or any other anatomical feature during the imaging scan so as to remove unwanted movement of the feature.

Posterior means situated at the back part of a structure; posterior is the opposite of anterior.

Precise as used herein means sharply defined and repeatable.

Precision means how close in value successive measurements fall when attempting to repeat the same measurement between two detectable features in the image field. In a normal distribution precision is characterized by the standard deviation of the set of repeated measurements. Precision is very similar to the definition of repeatability.

The prostate is a compound tubuloalveolar exocrine gland of the male reproductive system. The function of the prostate is to secrete a slightly alkaline fluid, milky or white in appearance, that in humans usually constitutes roughly 30% of the volume of the semen The pulse transit time across a region of the eye is the time it takes a sound pulse to traverse the region.

A pulser/receiver board carries the electronics required 1) to shape the electrical pulse to drive the ultrasound transducer; 2) to receive the return signal from the ultrasound pulse engaging the target; and 3) to isolate the stronger driver pulse from the much weaker received pulse.

Refractive means anything pertaining to the focusing of light rays by the various components of the eye, principally the cornea and lens.

Registration as used herein means aligning.

Scan head means the mechanism that comprises the ultrasound transducer, the transducer holder and carriage as well as any guide tracks that allow the transducer to be moved relative to the positioner. Guide tracks may be linear, arcuate or any other appropriate geometry. The guide tracks may be rigid or flexible. Normally, only the scan head is moved during a scan.

Sector scanner is an ultrasonic scanner that sweeps a sector like a radar. The swept area is pie-shaped with its central point typically located near the face of the ultrasound transducer.

A specular surface means a mirror-like surface that reflects either optical or acoustic waves. For example, an ultrasound beam emanating from a transducer will be reflected directly back to that transducer when the beam is aligned perpendicular to a specular surface.

Swept beam liquid interface ultrasound technology is an ultrasound technology wherein the transducer is moved in a prescribed path during scanning and wherein the ultrasound beam travels through a liquid medium from transducer face to the tissue being imaged. Swept beam liquid interface ultrasound technology is distinct from array based ultrasound technology.

Tissue means an aggregate of cells usually of a particular kind together with their intercellular substance that form one of the structural materials of a plant or an animal and that in animals include connective tissue, epithelium, muscle tissue, and nerve tissue.

A track or guide track is an apparatus along which another apparatus moves. In an ultrasound scanner or combined ultrasound and optical scanner, a guide track is an apparatus along which one or more ultrasound transducers and/or optical probes moves during a scan.

Trans-rectal ultrasound is used to create an image of organs in the pelvis by a probe inserted into the rectum. The most common usage for transrectal ultrasound is for the evaluation of the prostate gland in men with elevated prostate specific antigen or prostatic nodules on digital rectal exam.

Tissue harmonic imaging exploits non-linear propagation of ultrasound through the body tissues. The high pressure portion of the wave travels faster than low pressure resulting in distortion of the shape of the wave. This change in waveform leads to generation of harmonics (multiples of the fundamental or transmitted frequency) from tissue. Typically, the 2nd harmonic is used to produce the image as the subsequent harmonics are of decreasing amplitude and hence insufficient to generate a proper image. These harmonic waves that are generated within the tissue, increase with depth to a point of maximum intensity and then decrease with further depth due to attenuation. Hence the maximum intensity is achieved at an optimum depth below the surface. Advantages over conventional ultrasound include: decreased reverberation and side lobe artifacts; increased axial and lateral resolution; increased signal to noise ratio; and improved resolution in patients with large body habitus.

Ultrasonic or ultrasound means sound that is above the human ear's upper frequency limit. When used for imaging an object like the eye, the sound passes through a liquid medium, and its frequency is many orders of magnitude greater than can be detected by the human ear. For high-resolution acoustic imaging in the eye, the frequency is typically in the approximate range of about 5 to about 80 MHz.

Ultrasound Bio Microscopy (UBM) is an imaging technique using hand-held ultrasound device that can capture anterior segment images using a transducer to emit short acoustic pulses ranging from about 20 to about 80 MHz. This type of ultrasound scanner is also called a sector scanner. The UBM method is capable of making qualitative ultrasound images of the anterior segment of the eye but cannot unambiguously make accurate, precision, comprehensive, measurable images of the cornea, lens or other components of the eye.

A vector refers to a single acoustic pulse and its multiple reflections from various eye components. An A-scan is a representation of this data whose amplitude is typically rectified.

Water equivalent as used herein means a fluid or a gel having the approximate acoustic impedance of water.

BRIEF DESCRIPTION OF THE DRAWINGS

The present disclosure may take form in various components and arrangements of components, and in various steps and arrangements of steps. The drawings are only for purposes of illustrating the preferred embodiments and are not to be construed as limiting the disclosure. In the drawings, like reference numerals may refer to like or analogous components throughout the several views.

FIGS. 12A and 12B are schematics of a revolver type swept beam transducer holder.

DETAILED DESCRIPTION OF THE DRAWINGS

In this disclosure, an apparatus and a method are described that are the basis for a rapid screening device for non-invasive, high quality imaging and treatment of the prostate. This method can also be applied to other body parts. The apparatus and method combine several known ultrasound imaging components and techniques such as precision eye scanners, annular array transducers, coded excitation and biharmonic tissue imaging in an innovative way to ensure high quality imaging and patient comfort and safety. An important aspect of this disclosure is the apparatus and method to position the patient and the scanning apparatus in a way that minimizes the transducer distance to the prostate gland while preserving patient comfort and minimizing or eliminating patient risk.

Precision Eye Scanner

An ultra sound scanning apparatus, as described for example, in U.S. Pat. No. 8,317,709 is comprised of a positioning mechanism and a scan head. The positioning mechanism has x, y, z and beta (rotation about its z-axis) positioning mechanisms which make it possible to position the scan head relative to the eye component of interest. This operation is carried out while the patient's eye is positioned in contact with an eyepiece attached to the scanner and while the patient's head is fixed relative to the scanner by a head rest or by the eyepiece or by a combination of both. Once the positioning mechanism is set, the only moving part relative to the eye component of interest is the scan head. The scan head may be comprised of only an arcuate guide track which is typically used to produce an ultrasound scan of the cornea and/or much of the anterior segment of an eye. The scan head may be comprised of only a linear guide track. In another embodiment, the scan head may be comprised of an arcuate guide track and a linear guide track that can be moved in a combination of linear and arcuate motions to produce an ultrasound scan of the entire anterior segment including much of the posterior surface of the lens. The movement of the positioner and scan head relative to patient's eye socket is precisely known at all times by a system of magnetic encoder strips.

The movement of the scan head relative to the eye component of interest is therefore known with precision and accuracy as long as the patient does not move their eye during the scan. A single scan can take less than a second. A sequence of scans can take several seconds. A patient's eye can move significantly even during a single scan, thus degrading the precision and accuracy of the scan. The usual procedure, when this occurs, is to re-scan the patient. In US Publication No. 20130310692 entitled "Correcting for Unintended Motion for Ultrasonic Eye Scans", a device and method of tracking any movement of the patient's eye, relative to the positioning mechanism, during a scan is described.

Ultrasound Eye Scanning Apparatus

Figure 1:
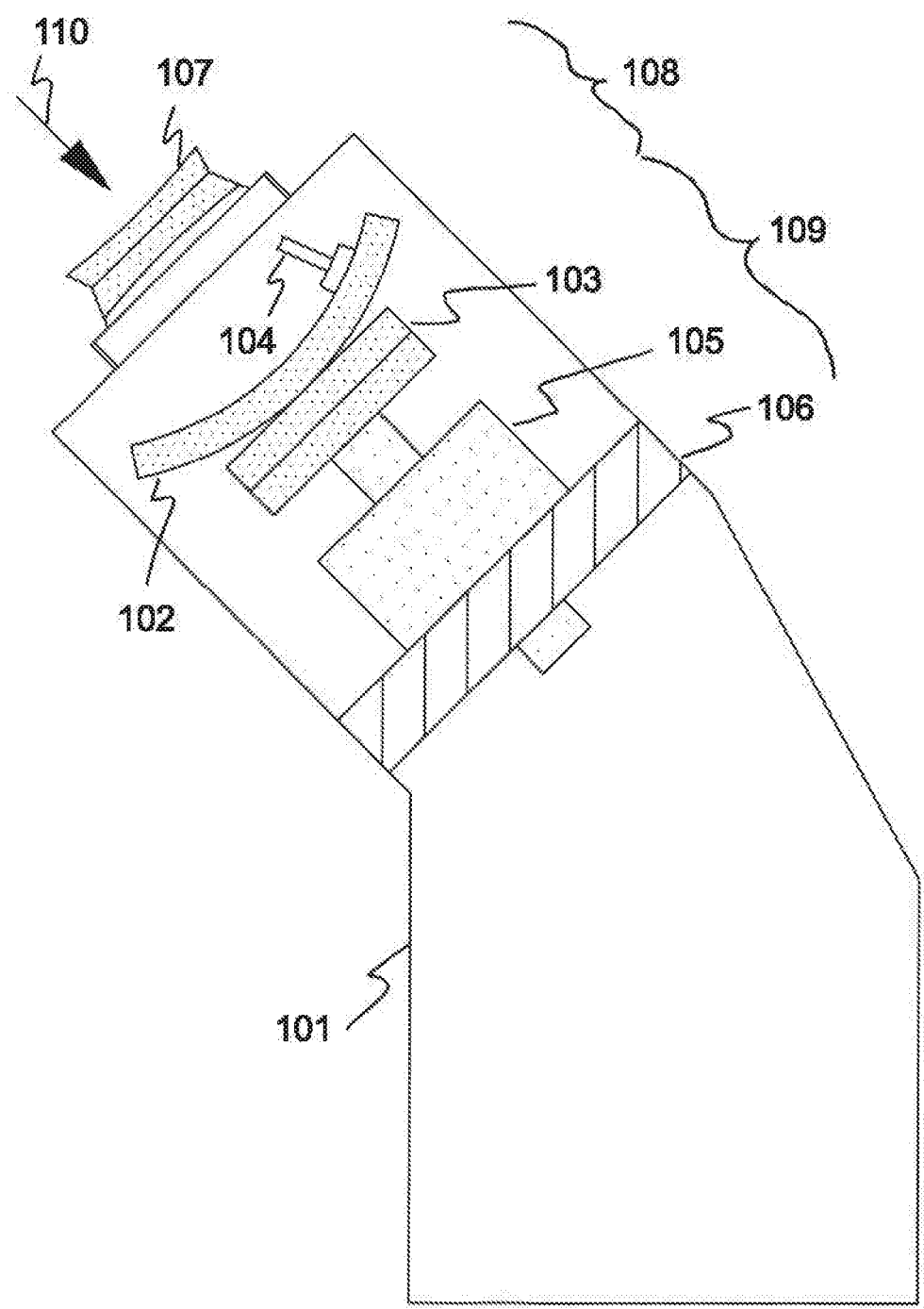
FIG. 1 is a schematic of a prior art arc scanner for imaging an eye using ultrasound.

FIG. 1 is a schematic of the principal elements of a prior art ultrasound eye scanning device such as described in U.S. Pat. No. 8,510,883. The scanning apparatus 101 of this example is comprised of a scan head assembly 108 (shown here as an arcuate guide 102 with scanning transducer 104 on a transducer carriage which moves back and forth along the arcuate guide track, and a linear guide track 103 which moves the arcuate guide track back and forth as described in FIG. 4), a positioning mechanism 109 comprised of an x-y-z and beta mechanisms 105 mounted on a base 106 which is rigidly attached to scanning apparatus 101, and a disposable eyepiece 107. The scanning machine 101 is typically connected to a computer (not shown) which includes a processor module, a memory module, and a video monitor. The patient is seated at the machine 101 with their eye engaged with disposable eyepiece 107. The patient is typically looking downward during a scan sequence. The patient is fixed with respect to the scanning machine 101 by a headrest system and by the eyepiece 107. The operator using, for example, a mouse and/or a keyboard and video screen inputs information into the computer selecting the type of scan and scan configurations as well as the desired type of output analyses. The operator, for example, again using a mouse and/or a keyboard, a video camera located in the scanning machine and video screen, then centers a reference marker such as, for example, a set of cross hairs displayed on a video screen on the desired component of the patient's eye which is also displayed on video screen. This is done by setting one of the cross hairs as the prime meridian for scanning. These steps are carried out using the positioning mechanism which can move the scan head in the x, x, z and beta space (three translational motions plus rotation about the z-axis). Once this is accomplished, the operator instructs computer using either a mouse and/or a keyboard to proceed with the scanning sequence. Now the computer processor takes over the procedure and issues instructions to the scan head 108 and the transducer 104 and receives positional and imaging data. The computer processor proceeds with a sequence of operations such as, for example: (1) with the transducer carriage substantially centered on the arcuate guide track, rough focusing of transducer 104 on a selected eye component; (2) accurately centering of the arcuate guide track with respect to the selected eye component; (3) accurately focusing transducer 104 on the selected feature of the selected eye component; (4) rotating the scan head through a substantial angle (including orthogonal) and repeating steps (1) through (3) on a second meridian; (5) rotating the scan head back to the prime meridian; (6) initiating a set of A-scans along each of the of selected scan meridians, storing this information in the memory module; (7) utilizing the processor, converting the A-scans for each meridian into a set of B-scans and then processing the B-scans to form an image associated with each meridian; (8) performing the selected analyses on the A-scans, B-scans and images associated with each or all of the meridians scanned; and (9) outputting the data in a preselected format to an output device such as storage disk drive or a printer. As can be appreciated, the patient's head must remain fixed with respect to the scanning machine 101 during the above operations when scanning is being carried out, which in a modern ultrasound scanning machine, can take several tens of seconds.

An eyepiece serves to complete a continuous acoustic path for ultrasonic scanning, that path extending in water from the transducer to the surface of the patient's eye. The eyepiece 107 also separates the water in which the patient's eye is immersed from the water in the chamber in which the transducer guide track assemblies are contained. The patient sits at the machine and looks down through the eyepiece 107 as shown by arrow 110. Finally, the eyepiece provides an additional steady rest for the patient and helps the patient to remain steady during a scan procedure.

As can be appreciated, the arcuate guide track used to image the eye has a radius of curvature similar to that of the cornea and anterior surface of the natural lens. If an arcuate guide track is used for imaging a prostate, for example, the radius of curvature can be appropriately adjusted by a combination of arcuate and linear motions such as described for example in U.S. Pat. No. 8,317,709. As can be further appreciated, the guide track can have another shape than arcuate or could, in principle, be made to flex in a precise way so as to custom fit a patient.

Annular Array Transducers, Coded Excitation and Tissue Harmonic Imaging

Single Element Ultrasound Transducer

Figure 2A:
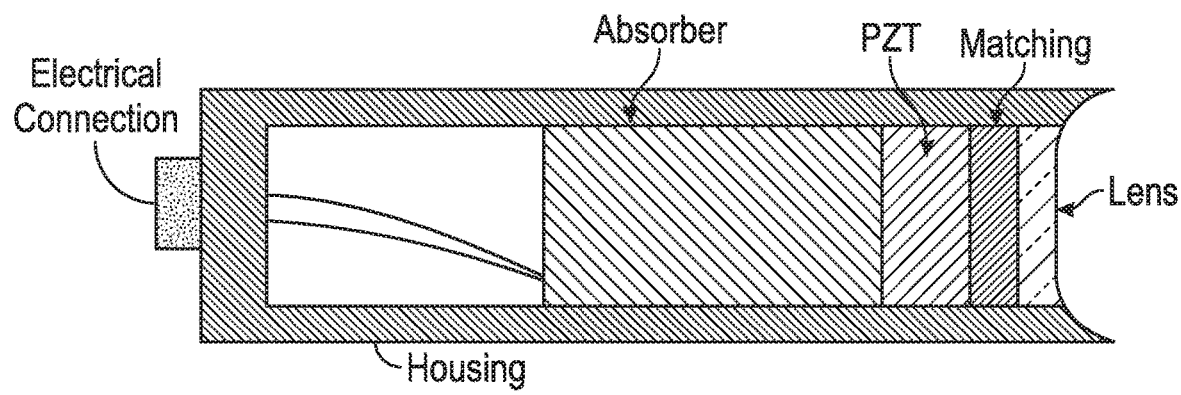
FIGS. 2A and 2B are schematics of prior art single and dual element ultrasound transducer assemblies.

A prior art single element or needle transducer is shown in FIG. 2a (taken from a slide show entitled "Ultrasound Transducers" by Ravi Managuli). This type of transducer is currently used in precision arc scanners such as described in FIG. 1, in the previous section and, for example, in U.S. Pat. Nos. 8,317,702 and 8,758,252. The single transducer element both transmits an ultrasound pulse and receives the echoed pulse.

Annular Array Ultrasound Transducers

Figure 2B:
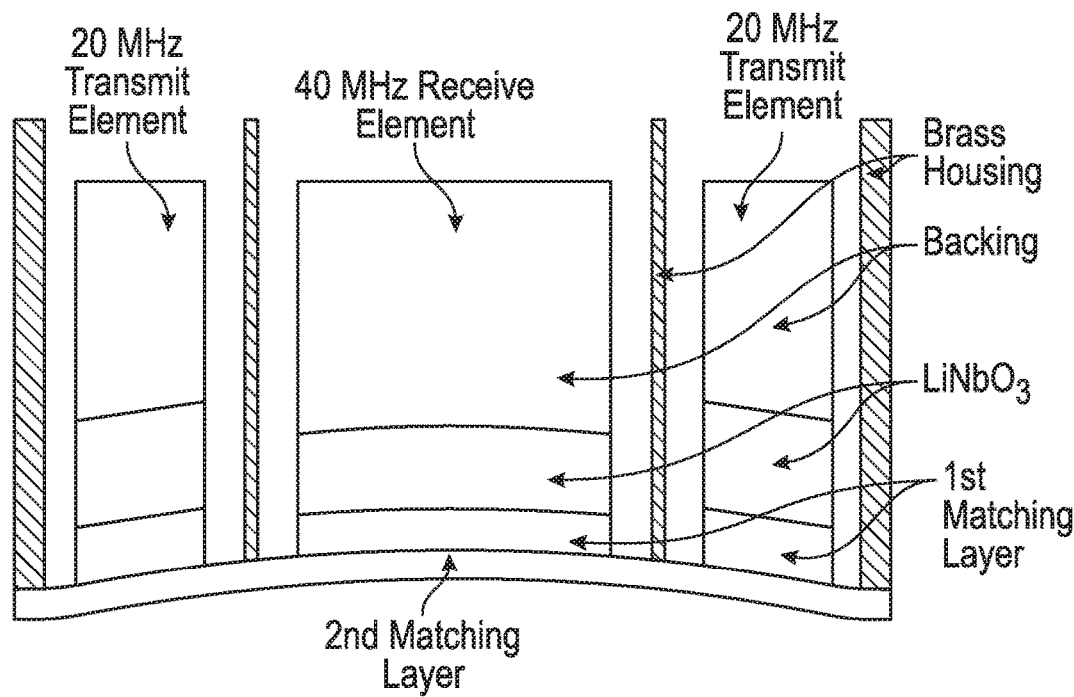

FIG. 2b is a schematic of a prior art dual element ultrasound transducer assembly as described in "20 MHz/40 MHz Dual Element Transducers for High Frequency Harmonic Imaging", Kim, Cannata, Liu, Chang, Silverman and Shung, IEEE Transactions on Ultrasonics, Ferroelectrics and Frequency Control, VOL. 55; NO. 12, December 2008. Both the annular element and the center element can transmit and receive ultrasound pulses independently. In another mode, the center element can transmit and receive a pulse at one frequency while the annular element can transmit and receive a separate pulse at a different frequency. In yet another mode, the annular element can transmit and receive a pulse at one frequency while the center element can receive the echoed pulse at a harmonic frequency of the transmitted pulse.

As discussed in the above reference, a concentric annular type dual element transducer was used for second harmonic imaging to improve spatial resolution and depth of penetration for ophthalmic imaging applications. The outer ring element was designed to transmit a 20 MHz signal and the inner circular element was designed to receive the 40 MHz second harmonic signal.

Tissue harmonic ultrasound imaging has been accepted as one of the standard imaging modalities in many applications since its introduction to medical ultrasound imaging in the 1990 s. Especially in cardiac and abdominal studies, tissue harmonic imaging is very often used for diagnostics along with fundamental imaging. By utilizing the second harmonic component of the received signal, images can be improved by reducing near field reverberation, decreasing phase aberration error, and improving border delineation.

In ophthalmology, imaging of the posterior segment which includes the retina, require improved spatial resolution and depth of penetration for proper diagnosis of retinal disease. This same second harmonic imaging technique can be used to improve imaging of, for example, the prostate.

Recently, broad band single element transducers operating at about 20 MHz have been used for imaging the posterior segment of the eye, but were limited in spatial resolution at that frequency. Unfortunately, transducers operating at 20 MHz cannot provide the spatial resolution needed to adequately delineate layers on the posterior segment of the human eye. Those operating in the higher frequency range do not provide sufficient depth of penetration such that the reflected signal can be detected above the noise floor. A concentric annular type dual element transducer for second harmonic imaging of the posterior segment of the eye wherein the outer ring element is used for transmit and the inner circular element for receive. A ring-shaped outer element produces higher side lobes than does a circular element of the same diameter, but this is to some degree compensated for by inherently lower side lobes in the harmonic compared with the fundamental.

Harmonic imaging with 20 MHz transmit and 40 MHz receive showed capability superior to that of fundamental imaging at 20 MHz to diagnose retinal disease in the posterior segment of the eye. The center frequencies of transmit and receive elements of dual element transducers can be further optimized to match the designed center frequencies to support a larger dynamic range. The aperture size of transmit and receive elements can also be optimized with further experimentation to achieve the best combination of transmit and receive efficiency.

There is a need to form a high precision image of the prostate from outside the patient's body wherein the resolution in sufficient to image, for example, cancerous lesions on the surface of the prostate. To achieve such images, coded excitation, tissue harmonic imaging, advanced transducers operating in the 10 MHz to 20 MHz range will be required to achieve a useable signal-to-noise reflection while being able to position the imaging transducer as close as possible to the prostate without risk or discomfort to the patient.

Figure 3:
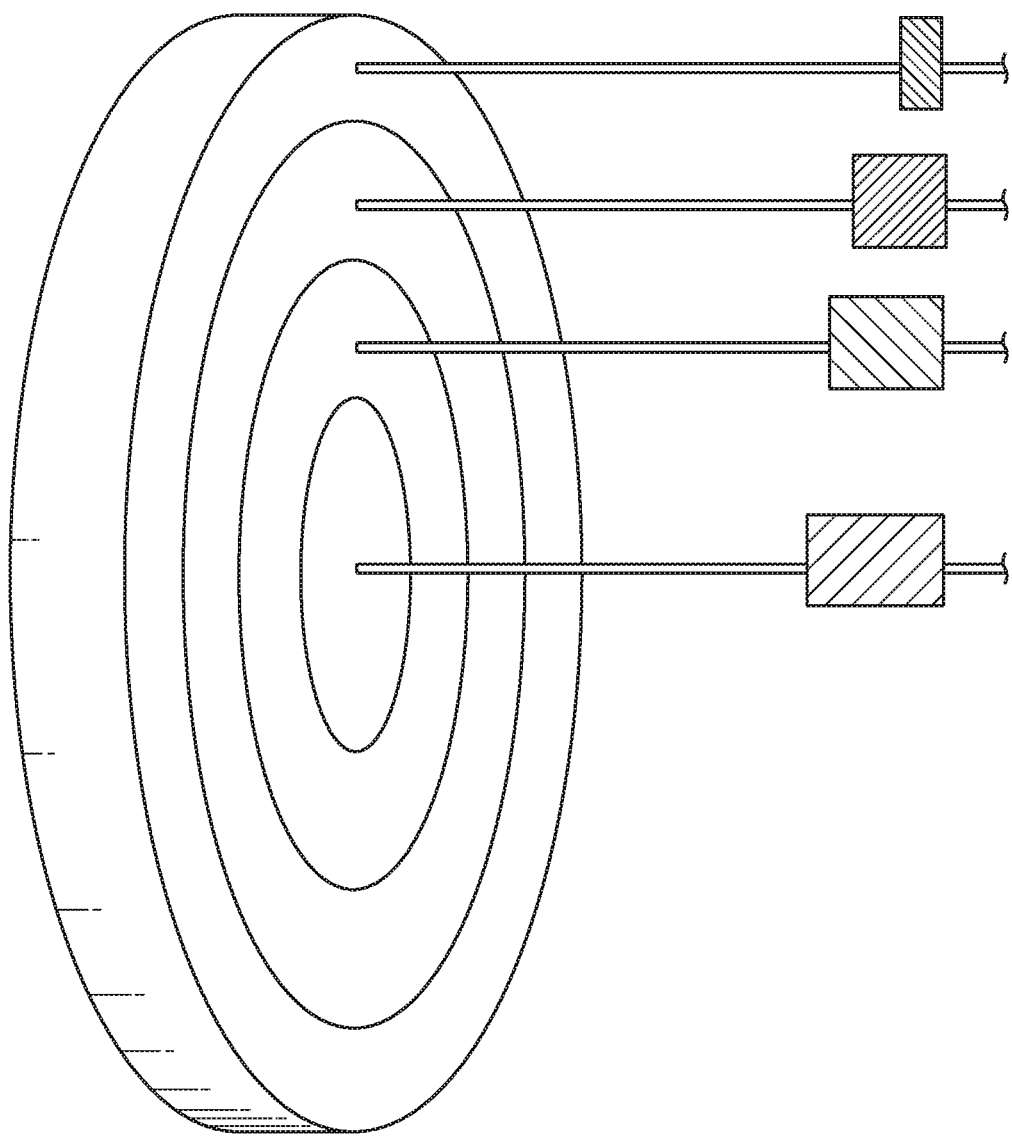
FIG. 3 is a schematic of the transducer face of a prior art multi-element ultrasound transducer configuration.

FIG. 3 is a schematic of the transducer face of a prior art multi-element ultrasound transducer configuration (taken from a slide show entitled "Ultrasound transducers by Ravi Managuli).

As discussed in "High-Frequency Ultrasonic Imaging of the Anterior Segment Using an Annular Array Transducer" Ronald H. Silverman, Jeffrey A. Ketterling and D. Jackson Coleman, Ophthalmology. April 2007, very-high-frequency ultrasound (VHFU>35 MHz) allows imaging of anterior segment structures of the eye with a resolution of less than 40 microns. The low focal ratio of VHFU transducers, however, results in a depth-of-field of less than 1,000 microns (1,000 microns is equal to 1-mm). A dual element high-frequency annular array transducer for ocular imaging shows improved depth-of-field sensitivity and resolution compared to conventional single element transducers.

As also discussed in the preceding reference, a spherically curved multiple annular array ultrasound transducer was tested wherein the array consisted of five concentric rings of equal area, had an overall aperture of 6 mm and a geometric focus of 12 mm. The nominal center frequency of all array elements was 40 MHz. An experimental system was designed in which a single array element was pulsed and echo data recorded from all elements. By sequentially pulsing each element, echo data were acquired for all 25 transmit/receive annular combinations. The echo data were then synthetically focused and composite images produced. This technology offers improved depth-of-field, sensitivity and lateral resolution compared to single element fixed focus transducers and dual element annular array transducers currently used for VHFU imaging of the eye.

Factors that impact upon the overall utility of ultrasound systems include resolution, penetration, speed (frames/second), sensitivity (signal/noise) and depth-of-field. Resolution generally improves (and penetration declines) with frequency. Very-high-frequency (>35 MHz) ultrasound (VHFU) provides an axial resolution of <40-μm, allowing exquisitely detailed depiction of anatomic structures. However, attenuation at this frequency is high, even in water, limiting clinical imaging in this frequency range to the anterior segment.

Annular arrays can be fabricated with no curvature (i.e., flat) with a spherical lens, or with a spherical geometry. While the principle of dynamic focusing is the same for all, spherically curved devices are advantageous compared to flat arrays because fewer elements are required to achieve the same improvement in depth of field. Spherical curvature also leads to better lateral resolution for two transducers of similar aperture and number of elements.

Current VHFU systems for evaluation of the anterior segment of the eye are constrained by their very limited depth of field. This results in reduced sensitivity and degraded resolution outside a focal zone that measures under one millimeter in axial extent. The performance of an annular array transducer operating in the same frequency range as current single-element UBM systems showed that this technology can provide a six-fold increase in depth of field. The improved resolution and sensitivity offered by annular array technology can therefore provide significant practical advantages in diagnostic imaging of anatomy and pathology. Furthermore, this technology can be readily extended to lower frequencies, such as 20-25 MHz, that would allow improved assessment of pathologies. In summary, a 40-MHz multiple annular array transducer for imaging of the anterior and posterior segments can be fabricated to achieve improved depth-of-field, sensitivity and lateral resolution.

Spatial resolution in an ultrasonic imaging system is dependent on beam and focal properties of the source, tissue attenuation, non-linearity of the medium, tissue inhomogeneity, and speed of sound speed in each tissue region.

In ultrasound, axial resolution is improved as the bandwidth of the transducer is increased, which typically occurs for higher center frequencies. However, the attenuation of sound typically increases as frequency increases, which results in a decrease in penetration depth. Therefore, there is an inherent tradeoff between spatial resolution and penetration in ultrasonic imaging.

One way to increase the penetration depth without reducing axial resolution is by increasing the excitation pulse amplitude. However, increased excitation amplitude results in increased pressure levels that could result in unwanted heating or damage to tissues. Therefore, increasing the excitation pulse amplitude is not always a viable solution, depending on the region being imaged. For example, regulations for ultrasound power and time duration are low for the eye relative to the heart.

Coded Excitation

Coded excitations are engineered excitation pulses that are capable of increasing the effective penetration depth of a transmitted signal in echo location imaging systems such as radar, sonar and ultrasound, by improving the signal-to-noise ratio (SNR).

An alternate solution to increase the penetration depth, as opposed to increasing the excitation pulse amplitude, would be to increase the excitation pulse duration by using coded excitation which increases the total transmitted energy and allows for the minimization of the transmitted peak power. However, increasing signal duration has the negative effect of decreasing the axial resolution of the ultrasonic imaging system.

In order to restore the axial resolution after excitation with a coded signal, pulse compression is used. Pulse compression can be realized by using one or more filtering methods. The main disadvantage of using coded excitation and pulse compression would be the introduction of range side lobes that can appear as false echoes in an image. The introduction of range side lobes is a detriment to ultrasonic image quality because it can reduce the contrast resolution. The main advantage for using coded excitation is that it is known to improve the echo signal-to-noise ratio by increasing the time/bandwidth product of the coded signal. This improvement in echo signal-to-noise results in greater depth of penetration in the range of a few centimeters for ultrasonic imaging and improved image quality. Furthermore, this increase in penetration depth allows the possibility of shifting to higher frequencies with larger bandwidths in order to increase the spatial resolution at depths where normally it would be difficult to image.

Ultrasound is a non-ionizing, non-invasive, real-time imaging method than other techniques such as magnetic resonance imaging. However, the finer resolution advantages offered by high frequency ultrasound are offset by limitations in penetration depth caused by frequency-dependent attenuation and limitations in depth-of-field when low f-number transducers are employed to improve cross-range resolution. Attenuation of ultrasound in tissue increases with frequency and, therefore, current uses of high frequency ultrasound are limited to applications that do not require deep penetration to image the tissue of interest. High frequency ultrasound image quality can be significantly improved by using two independent approaches.

The first approach uses synthetic focused annular arrays with overall apertures similar to typical spherically focused transducers to increase depth-of-field. The radial symmetry of annular arrays leads to a high-quality radiation pattern while employing fewer elements than linear or phased arrays. However, annular arrays need to be mechanically scanned to obtain a 2D image.

An annular array ultrasound transducer can consist of a two element array such as shown in FIG. 2b or a multi-element array such as shown in FIG. 3.

As an example, concentric annular type dual element transducers for second harmonic imaging at 20 MHz/40 MHz were designed to improve spatial resolution and depth of penetration for ophthalmic imaging applications. The outer ring element may be designed to transmit the 20 MHz signal and the inner circular element may be designed to receive the 40 MHz second harmonic signal. These types of annular arrays are described, for example, in "20 MHz/40 MHz Dual Element Transducers for High Frequency Harmonic Imaging, Kim, Cannata, Liu, Chang, Silverman and Shung, IEEE Transactions on Ultrasonics, Ferroelectrics and Frequency Control, Vol. 55; NO. 12, December 2008.

A multi-annuli array transducer is described in "Chirp Coded Excitation Imaging with a High-frequency Ultrasound Annular Array", Mamou, Ketterling and Silverman, IEEE Trans Ultrasonics, Ferroelectrics and Frequency Control. 28 Feb. 2008. The array consists of five equal-area annuli with a 10-mm total aperture and a 31-mm geometric focus.

The second high frequency ultrasound imaging approach uses coded excitations (i.e., engineered excitation pulses) that are capable of increasing the effective penetration depth by improving the signal-to-noise ratio. Resolution and penetration depth are critically important for medical ultrasound imaging. Normally, these two properties present a tradeoff, in which one property can be improved only at the expense of the other. However, it has been demonstrated that coded excitation is capable of extending the limit associated with this tradeoff. Coded excitation permits the signal-to-noise ratio to be increased through appropriate encoding on transmit and decoding on receive. In a published study, linear chirp signals were used to excite an annular array transducer. The objectives of this study were to demonstrate that chirp annular array imaging can lead to better image quality than current state-of-the-art high frequency ultrasound images. The described methods are general and are applicable to a vast range of clinical applications, including ophthalmological, dermatological, and gastrointestinal imaging.

To appreciate how coded excitation can increase signal-to-noise ratio (SNR), white noise can be added to the received response. Typically, a response had an SNR of 45 dB, which is in the range of most ultrasound imaging systems. Chirp excitations led to an increase in SNR of greater than 14 dB.

Figure 4:
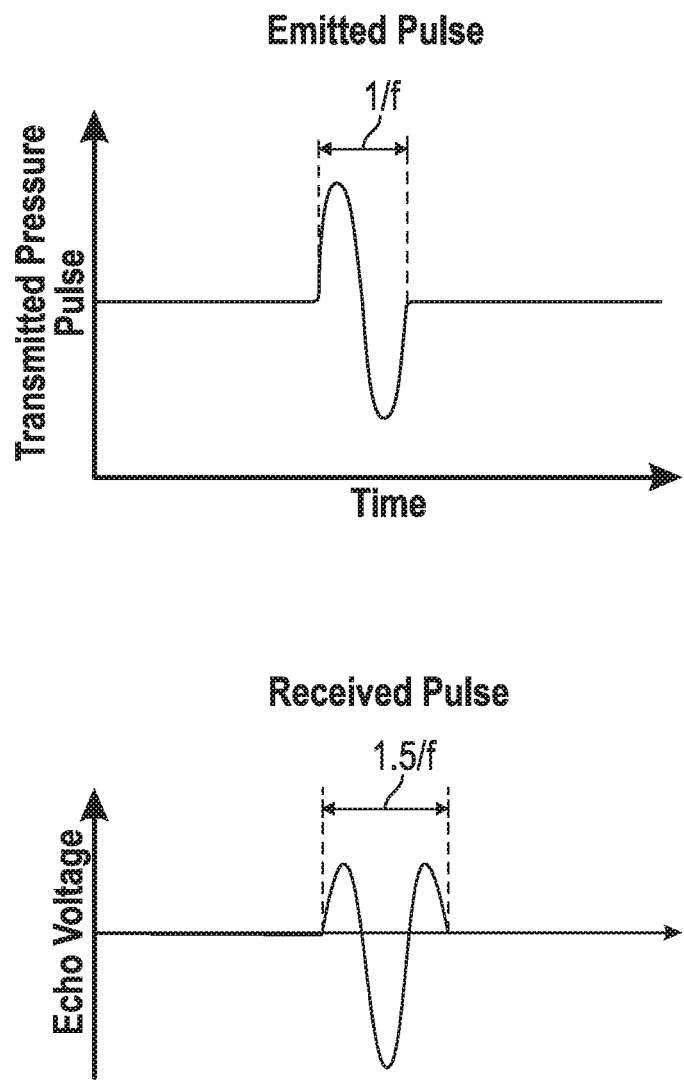
FIG. 4 is an example of a simple emitted and received ultrasound pulse waveform.

FIG. 4 is an example of a simple emitted and received ultrasound pulse waveform that is used, for example, in the precision arc scanner described above which uses a single element transducer such as shown in FIG. 2a taken from "Ultrasonography of the Eye and Orbit", Second Edition, Coleman et al, published by Lippincott Williams & Wilkins, 2006.

Figure 5:
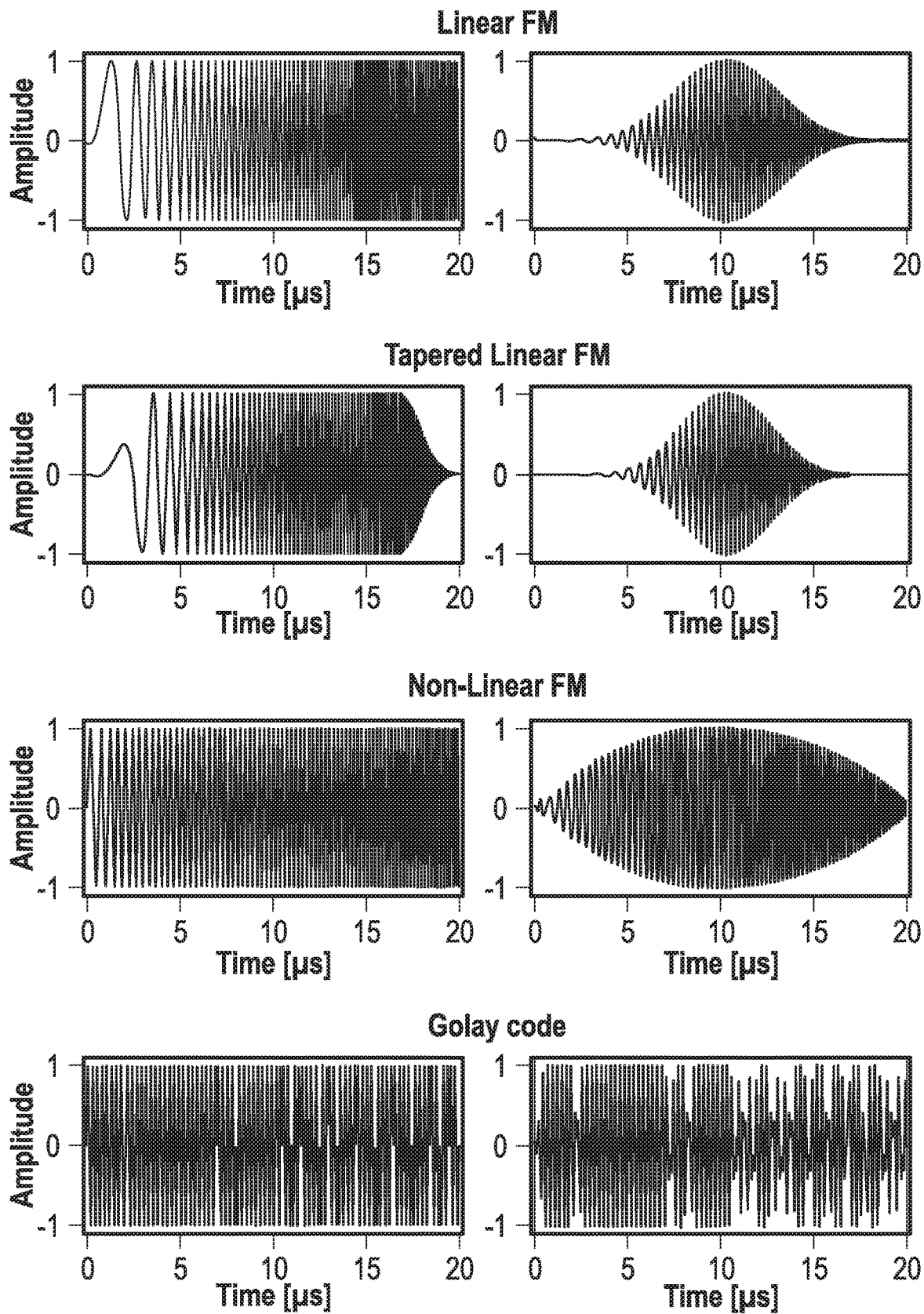
FIG. 5 shows examples of several known emitted chirp ultrasound pulse waveforms.

FIG. 5 shows examples of several emitted coded excitation ultrasound pulse waveforms. This figure was taken from "Use of Modulated Excitation Signals in Medical Ultrasound. Part I: Basic Concepts and Expected Benefits", Misaridis and Jensen, IEEE Transactions on Ultrasonics, Ferroelectrics, and Frequency Control, vol. 52, no. 2, February 2005.

Tissue Harmonic Imaging

Tissue harmonic imaging exploits non-linear propagation of ultrasound through body tissues. The high pressure portion of the wave travels faster than low pressure resulting in distortion of the shape of the wave. This change in waveform leads to generation of harmonics (multiples of the fundamental or transmitted frequency) from the tissue. Typically, the second harmonic is used to produce the image as the subsequent harmonics are of decreasing amplitude and hence insufficient to generate a proper image. These harmonic waves that are generated within the tissue, increase with depth to a point of maximum intensity and then decrease with further depth due to attenuation. Hence the maximum intensity is achieved at an optimum depth below the surface. Advantages over conventional ultrasound include: decreased reverberation and side lobe artifacts; increased axial and lateral resolution; increased signal-to-noise ratio; and improved resolution in patients with large body habitus.

Tissue harmonic ultrasound imaging has been accepted as one of the standard imaging modalities in many applications since its introduction to medical ultrasound imaging in the 1990s. Especially in cardiac and abdominal studies, tissue harmonic imaging is very often used for diagnostics along with fundamental imaging. By utilizing the second harmonic component of the received signal, images can be improved by reducing near field reverberation, decreasing phase aberration error, and improving border delineation.

Ultrasound tissue harmonic imaging utilizing nonlinear distortion of the transmitted frequencies within the body is useful for producing a sharper, higher-contrast ultrasound image than that of the fundamental frequency. Due to its improved conspicuity (the property of being clearly discernible) and border definition, tissue harmonic imaging has been widely used for detecting subtle lesions in, for example, the thyroid and breast, and visualizing technically-challenging patients with high body mass index. However, compared to conventional ultrasound imaging, tissue harmonic imaging suffers from the low signal-to-noise ratio, resulting in limited penetration depth. The signal-to-noise ratio in tissue harmonic imaging can be substantially increased by utilizing coded excitation techniques, such as described previously in this disclosure. In coded tissue harmonic imaging, similar to conventional coded excitation, specially-encoded ultrasound signals (for example, Barker, Golay and chirp) are transmitted, and then back-scattered receive signals containing fundamental and harmonic frequencies are selectively decoded via pulse compression.

Tissue Harmonic Imaging and Coded Excitation Together

Tissue harmonic imaging allows one to obtain medical ultrasound images with higher signal-to-noise ratio and higher spatial resolution. Tissue harmonic imaging and coded excitation together have been applied to medical ultrasound imaging. Coded excitation can overcome the trade-off between spatial resolution and penetration, which occurs when using a conventional transmitted pulse. For example, a chirp signal is frequently used for medical ultrasound imaging. A combination of coded excitation and tissue harmonic imaging has been found to produce superior ultrasound images.

As discussed in "Use of Modulated Excitation Signals in Medical Ultrasound. Part I: Basic Concepts and Expected Benefits", Misaridis and Jensen, IEEE Transactions on Ultrasonics, Ferroelectrics, and Frequency Control, vol. 52, no. 2, February 2005, tissue harmonic imaging allows one to obtain medical ultrasound images with higher signal-to-noise ratio and higher spatial resolution. Tissue harmonic imaging and coded excitation applied to medical ultrasound imaging has been investigated. Coded excitation can overcome the trade-off between spatial resolution and penetration, which occurs when using a conventional transmitted pulse. For example, a chirp signal is frequently used for medical ultrasound imaging. A combination of coded excitation and tissue harmonic imaging has been found to produce superior ultrasound images.

As discussed in "Coded Excitation for Ultrasound Tissue Harmonic Imaging", Song, Kim, Sohn, Song and Yoo. Received in revised form 18 Dec. 2009 Ultrasonics journal homepage: www.elsevier.com/locate/ultras, it is shown how coded signals, when processed with a matched filter, can be evaluated in the presence of ultrasonic attenuation using ambiguity functions. It is shown that if matched-filter receiver processing is used, the compressed output is not the autocorrelation function of the code, but a cross section of the ambiguity function for a certain frequency downshift. Therefore, the AF of the transmitted waveform ought to have desired properties in the entire delay-frequency shift plane. The criteria of selecting the appropriate coded waveforms and receiver processing filters have been discussed in detail. One of the main results is the conclusion that linear FM signals have the best and most robust features for ultrasound imaging. Other coded signals such as nonlinear FM and binary complementary Golay codes also have been considered and characterized in terms of SNR and sensitivity to frequency shifts. These results have been demonstrated. It is found that, in the case of linear FM signals, a SNR improvement of 12 to 18 dB can be expected for large imaging depths of attenuating media, without any depth dependent filter compensation. In contrast, nonlinear FM modulation and binary codes are shown to give a SNR improvement of only 4 to 9 dB when processed with a matched filter. It was shown how the higher demands on the codes in medical ultrasound can be met by amplitude tapering of the emitted signal and by using a mismatched filter during receive processing to keep temporal side lobes below 60 to 100 dB.

High-Intensity Focused Ultrasound

High-intensity focused ultrasound (HIFU) is a non-invasive therapeutic technique that uses non-ionizing ultrasonic waves to heat tissue. HIFU can be used to increase the flow of blood or to destroy tissue, such as tumors, through a number of mechanisms. The technology is similar to ultrasonic imaging, although practiced at lower frequencies and higher acoustic power. Acoustic lenses may be used to achieve the necessary intensity at the target tissue without damaging the surrounding tissue. "Systematic Review of the Efficacy and Safety of High-Intensity Focussed Ultrasound for the Primary and Salvage Treatment of Prostate Cancer", M. Warmuth, T. Johansson, P. Mad, European Urology 58 (2010) 803-815, Sep. 17, 2010.

A typical HIFU transducer has a diameter of about 19 mm with a center frequency of about 5 MHz, a focal length of about 15 mm and a focal intensity of about 200 W/mm$^2$. Another typical HIFU transducer has a diameter of about 60 mm with a center frequency of about 1 MHz, a focal length of about 75 mm and a focal intensity of about 17 W/mm$^2$.

Present Disclosure

The present disclosure, which uses features described above, illustrates two apparatuses for utilizing a precision ultrasound scanner to make an image of a prostate for a male patient without causing undue patient discomfort or health risk due to the activity of the physician or, for example, a device such as a trans-rectal probe. A feature of each apparatus is that the scanner positioning mechanism and scan head are completely immersed in water. The patient sits on the instrument with his rectal area over an acoustically transparent window (the window may also be optically transparent). The ultrasound transducer is positioned as close to the underside of the window as possible prior to initiating a sequence of scans. The ultrasound transducer is centered on the region closest to the patient's prostate, for example, using either ultrasound or optical means to center on the rectum such that the ultrasound pulses are aimed at the prostate through the perineum.

Figure 6:
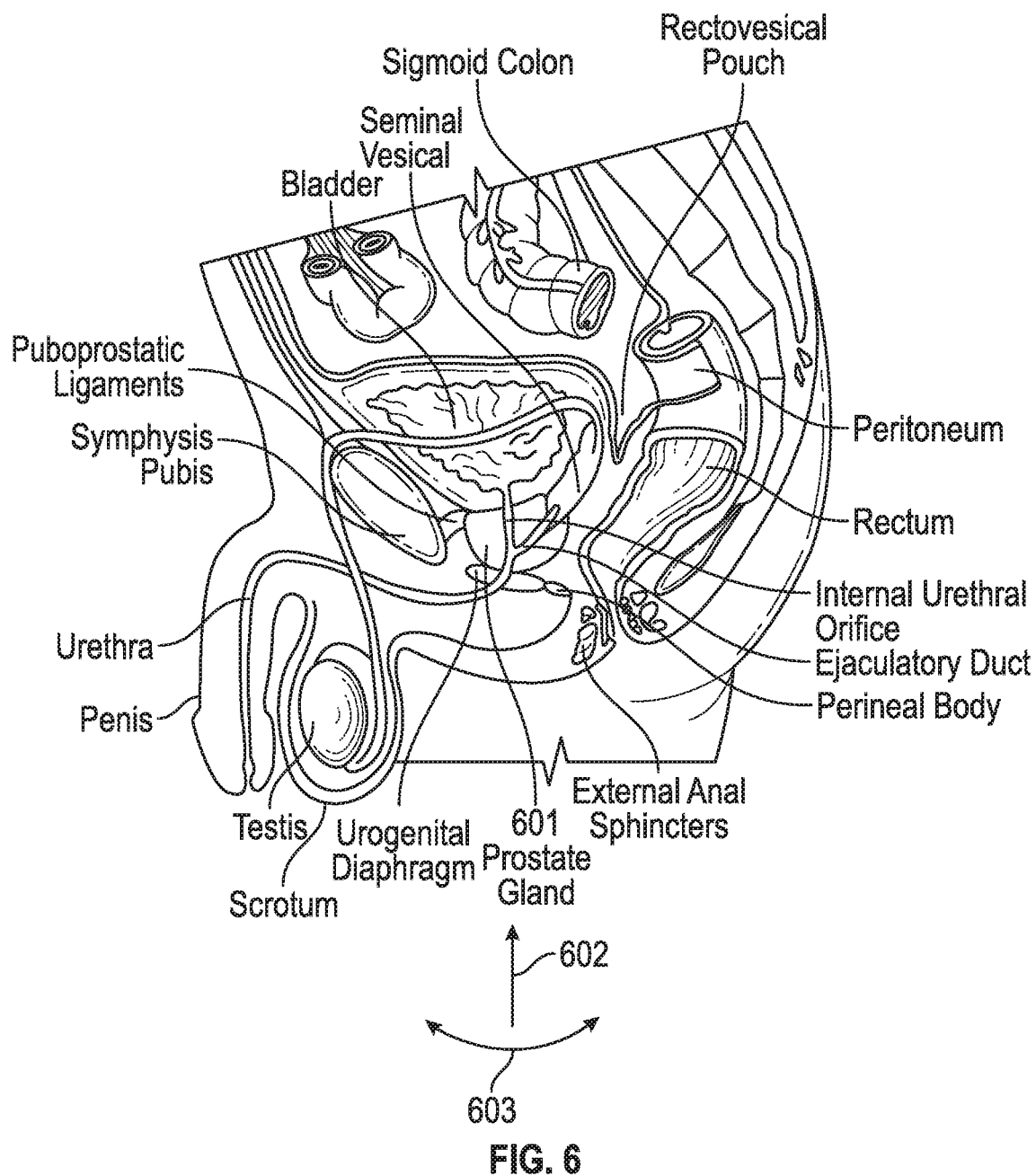
FIG. 6 illustrates the male perineum and the direction of the transducer pulse of the present disclosure.

FIG. 6 illustrates the principal features of in the male perineum and the direction 602 from which the transducer pulse is emitted. The prostate gland 601 sits just below the bladder. The ultrasound transducer is moved along an arcuate or linear guide track. An arcuate guide track is preferred since the transducer can maintain an approximately constant distance from the prostate glans 601 by moving in a curved motion 603. By imaging from below the patient through the perineum, the ultrasound emitted and reflected pulses do not pass through any bony structures that would severely attenuate ultrasound pulses.

The patient sits on a thin bag of acoustically transparent gel (the gel may also be optically transparent) so that the transmission path from the ultrasound transducer to the prostate is substantially of the same acoustic impedance (the gel bag conforms to the window over the scanner and to the patient's anatomy).

The male prostate is often described as the size of a walnut or golf ball. The prostate gland is approximately 40 mm by 30 mm by 20 mm. As described in the present disclosure, the positioning of the patient for scanning is designed to place the ultrasound transducer approximately 50 to 130 mm from the nearest surface of the prostate.

Figure 7A:
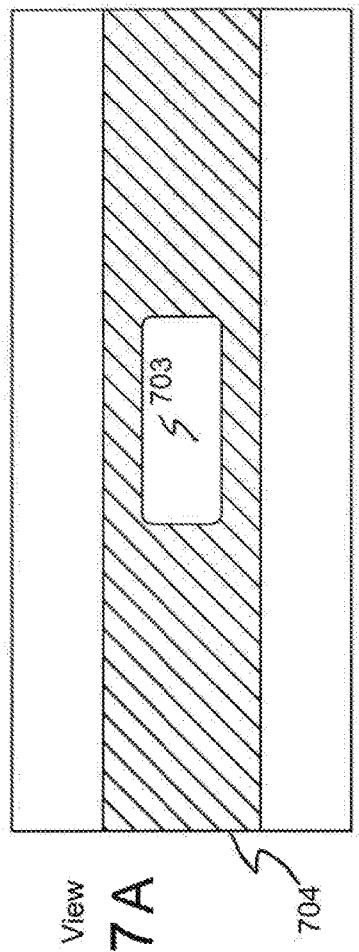
FIGS. 7A-7C are schematics of a saddle seating apparatus with an ultrasound scanner inside.
Figure 7C:
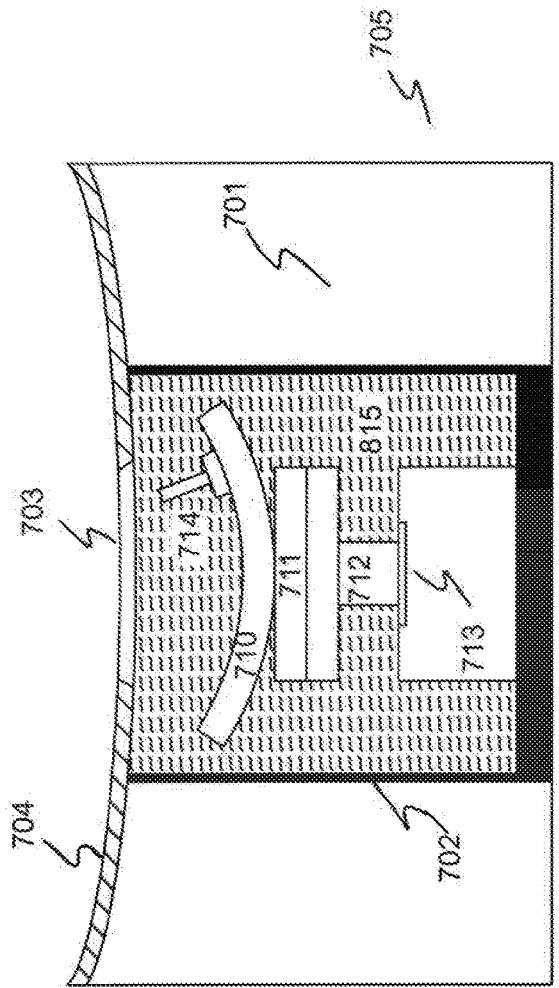
Figure 7B:
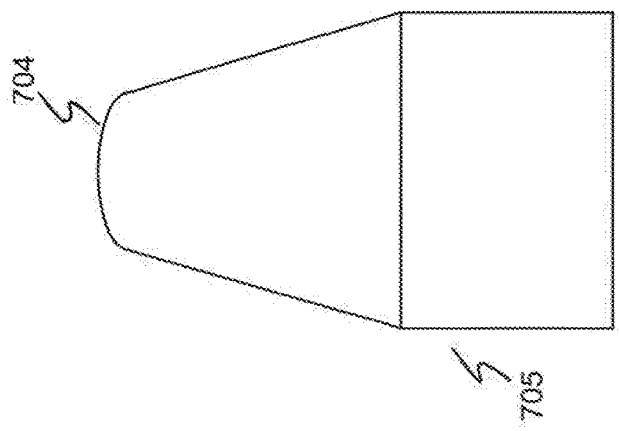

FIGS. 7A-7C are schematics of a saddle seating apparatus 705 with an ultrasound scanner positioned inside the saddle apparatus. The patient is seated on saddle 704 with his rectal area over window 703. The ultrasound scanner apparatus is contained within a water-tight enclosure 702 which is filled with water 715. The other instrument volume 701 is open to the ambient air and may contain a computer, power supplies and fluidics modules.

The ultrasound scanner apparatus is comprised of a positioning mechanism 712 which can be moved vertically (along the z-axis) as well as in both lateral directions (x and y-axes) on slider 713. The ultrasound scanner apparatus is also comprised of a scan head which is further comprised of either or both a linear guide track 711, an arcuate guide track 710 on which the ultrasound transducer and its carriage 714 moves as discussed above. The ultrasound transducer can be a single element needle probe, an annular array probe, and/or a linear transducer array. The scanning apparatus can also include a video camera (not shown) that provides an optical image of the outside of the body part being scanned by the ultrasound probe. This can enable a healthcare professional to more accurately position the ultrasound transducer relative to the target to be imaged. The positioning mechanism may able to tilt. Tilting means changing the tilt angle of the positioner mechanism and scan head by rotating about the x-axis in the y-z plane. The arcuate guide track is aligned with the x-axis such that the transducer carriage moves back and forth in an arc aligned with the x-axis. A linear guide track would also be aligned with the x-axis such that the transducer carriage moves back and forth parallel to the x-axis.

Figure 8A:
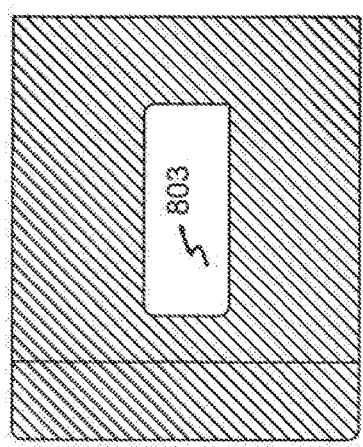
FIGS. 8A-8C are schematics of a bowl seating apparatus with an ultrasound scanner inside.
Figure 8C:
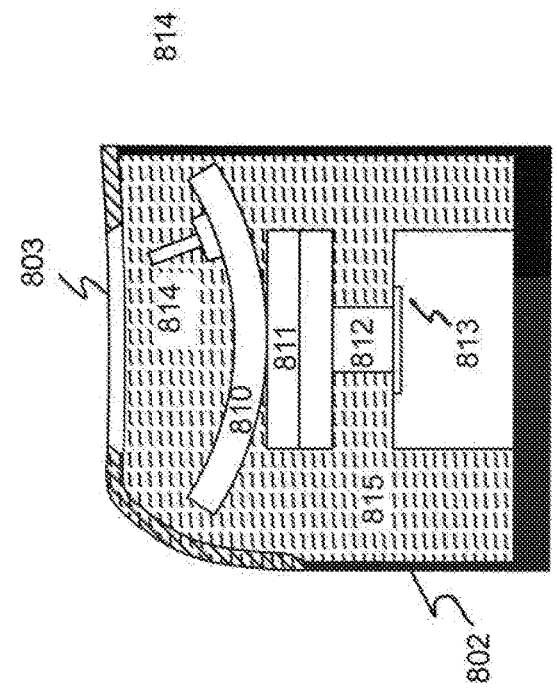
Figure 8B:
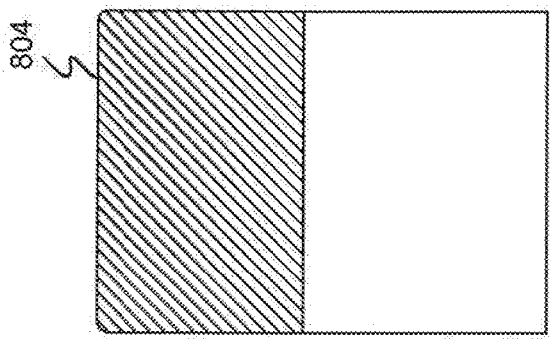

FIGS. 8A-8C are schematics of a bowl seating apparatus with an ultrasound scanner 803 inside. Functionally, this apparatus is similar to the apparatus of FIGS. 7A-7C. Functionally, this apparatus is similar to the apparatus of FIGS. 7A-7C. FIGS. 8A-8C are schematics of a saddle seating apparatus 814 with an ultrasound scanner positioned inside the saddle apparatus. The patient is seated on saddle 804 with his rectal area over window 803. The ultrasound scanner apparatus is contained within a water-tight enclosure 802 which is filled with water 815. The other instrument volume 801 is open to the ambient air and may contain a computer, power supplies and fluidics modules.

The transparent window 703 or 803 can be detachable window and is connected to and embedded in the saddle of the scanning instrument container. The window is typically made from a material that can transmit optical and acoustic energy. The window may be round, elliptical or square with rounded corners such that the window can allow the scanner to scan the selected body part of the patient.

The ultrasound scanner apparatus is comprised of a positioning mechanism 812 which can be moved vertically (along the z-axis) as well as in both lateral directions (x and y-axes) on slider 813. The ultrasound scanner apparatus is also comprised of a scan head which is further comprised of either or both a linear guide track 811, an arcuate guide track 810 on which the ultrasound transducer and its carriage 814 moves as discussed above.

As noted, the patient sits on a thin bag (not shown) of acoustically transparent gel (the gel may also be optically transparent) so that the transmission path from the ultrasound transducer to the prostate is substantially of the same acoustic impedance (the gel bag conforms to the window over the scanner and to the patient's anatomy). The thin bag is positioned between the seated patient (who is seated on the saddle 704 or 804) and the acoustically transparent window 703 or 803 and conforms to the detachable window in the saddle and to the body part being scanned by the ultrasound probe to form the continuous acoustic transmission path to and from the target feature of the patient. The disposable bag of gel is typically placed over the window, and the patient commonly sits on the bag so that the gel is in contact with the window and with the patient's body. Alternately, the disposable and deformable container could, for example, be a pair of shorts with the disposable and deformable container of clear gel sewn into the crotch area of the shorts.

As will be appreciated, the saddle 704 or 804, in other embodiments, can be bowl-shaped to act as a shallow reservoir for water in which the patent is seated. In this embodiment, no gel is required. A disadvantage of this approach is that the water will need to be removed by a pump and attached piping or by a stop cock with gravity flow through piping after each patient is imaged. The thin bag of acoustically transparent gel, on the other hand, can simply be removed and discarded by a health care professional after each patient is imaged.

The scanning instrument container formed by a saddle can comprise stirrups (not shown) for the patient's feet and handle bars (not shown) for the patient's hands. The stirrups and handle bars can allow the patient to lean forward to assume an optimal position for scanning and assist patients in sitting and standing.

A computer (not shown), comprising input and/or output devices, controls the scanning apparatus (controls the positioning mechanism, the scan head, the transmitting and receiving of the ultrasound probe and/or the manipulation of A-scans to form a B-scan of the prostate gland) as discussed above.

The configuration of the scanning instrument container formed by a saddle or bowl on which the patient sits can allow the scan to be conducted upwards through the patient's perineum thereby providing a short transmission/receiving path to the prostate while remaining a non-invasive procedure that minimizes patient discomfort and risk of infection. This configuration, can not only provide a continuous fluid path of substantially similar acoustic transmission properties from the ultrasound transducer to the body part being scanned but also substantially minimize the distance between the ultrasound transducer to the body part being scanned.

The frequency characteristic of the ultrasound probe and the peak power of the transducer emissions are commonly selected so that an image of the prostate can be formed when the prostate is about 50 to 130 millimeters from the face of the transducer element. The center frequency of the probe may be in the range of about 10 MHz to about 40 MHz to provide the required image resolution.

The peak power output of the ultrasound probe can be within the limits established by the FDA or other regulatory body. For example, a spatial-peak pulse-average intensity of 94 mW/cm2 and a spatial-peak temporal-average intensity of 190 W/cm2 would be allowable under 2008 FDA guidelines. This compares to a spatial-peak pulse-average intensity of 17 mW/cm2 and a spatial-peak temporal-average intensity of 28 W/cm2 allowable under current FDA guidelines for ophthalmic imaging. This represents a six-fold increase in transducer power over allowable ophthalmic imaging transducer power (a scan depth of about 6 to 7.5 mm for anterior segment scanning of the human eye and a scan depth of about 25 mm for retinal scanning of the human eye).

In operation, the scanning instrument container of the bowl seating apparatus is filled with distilled water; the disposable and deformable container of clear gel is placed on the saddle; the patient sits on the container of clear gel in preparation for scanning (or the patient puts on the disposable shorts and sits on the saddle or bowl); the probe is centered on the arcuate guide track; the video camera is used to position the ultrasound probe on the area of interest of the patient (such as by the positioner assembly moving the scan head into position for scanning); and scans are then made at different depths of focus and at different meridians (by rotating the arcuate guide assembly about its beta axis or by tilting the arcuate guide assembly). Scans may also be made through different sections of the prostate by translating the arcuate guide assembly with the positioner mechanism.

Figure 9A:
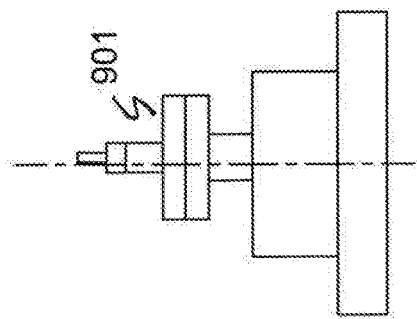
FIGS. 9A-9F illustrates modes of positioning a scan head with respect to a patient.
Figure 9B:
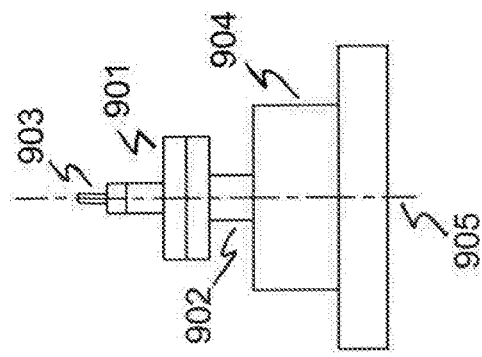
Figure 9C:
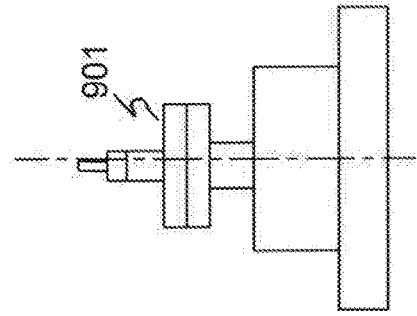

FIGS. 9A-9F illustrate modes of positioning a scan head with respect to a patient. FIGS. 9A-9F show a series of end views of the seating apparatus shown in FIGS. 7A-7C for example. FIGS. 9A-9C illustrate a translational positioning of the scan head 901 with respect to the vertical centerline. This mode of scanning allows a series of images showing vertical cuts through the prostate gland. Using the positioning accuracy and resolution of the eye scanning instrument described in FIG. 1, lateral scan head movements of 5 to 10 microns (0.005 to 0.01 mm) are routinely used. Thus many closely spaced vertical cuts through the prostate gland can be made with the prostate scanning instrument moving in its translational mode. As noted previously, the prostate gland is approximately 40 mm by 30 mm by 20 mm. For example, if desired, vertical scans can be made at a lateral spacing of every 0.01 mm over a lateral range of about 5 to about 10 mm on either side of the vertical centerline.

Figure 9D:
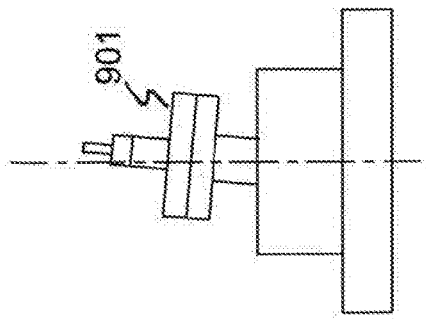
Figure 9E:
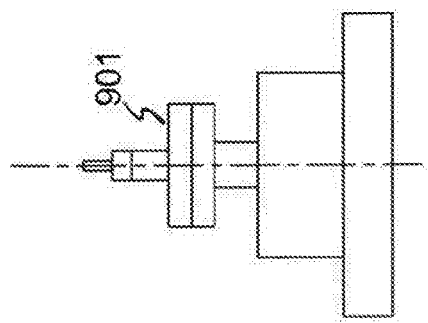
Figure 9F:
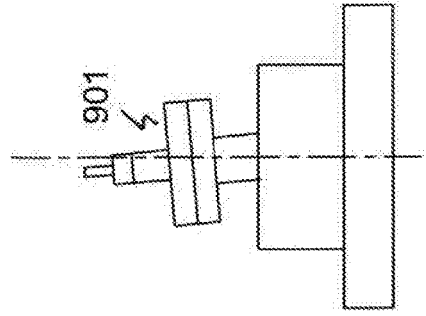

FIGS. 9D-9F illustrate a tilt positioning of the scan head 901 with respect to the vertical centerline. This mode of scanning allows a series of images showing cuts through the prostate gland that are at a slight angle to either side of the vertical centerline. Using the positioning accuracy and resolution of the eye scanning instrument described in FIG. 1, angular scan head movements of 1 degree are routinely used. Thus many closely spaced angular cuts through the prostate gland can be made with the prostate scanning instrument moving in its tilt mode. As noted previously, the prostate gland is approximately 40 mm by 30 mm by 20 mm. For example, if desired, vertical scans can be made at an angular spacing of every 1 degree over an included angular range of about 10 to about 25 degrees, depending on the size of the prostate gland and the distance from the ultrasound transducer to the prostate.

Figure 10:
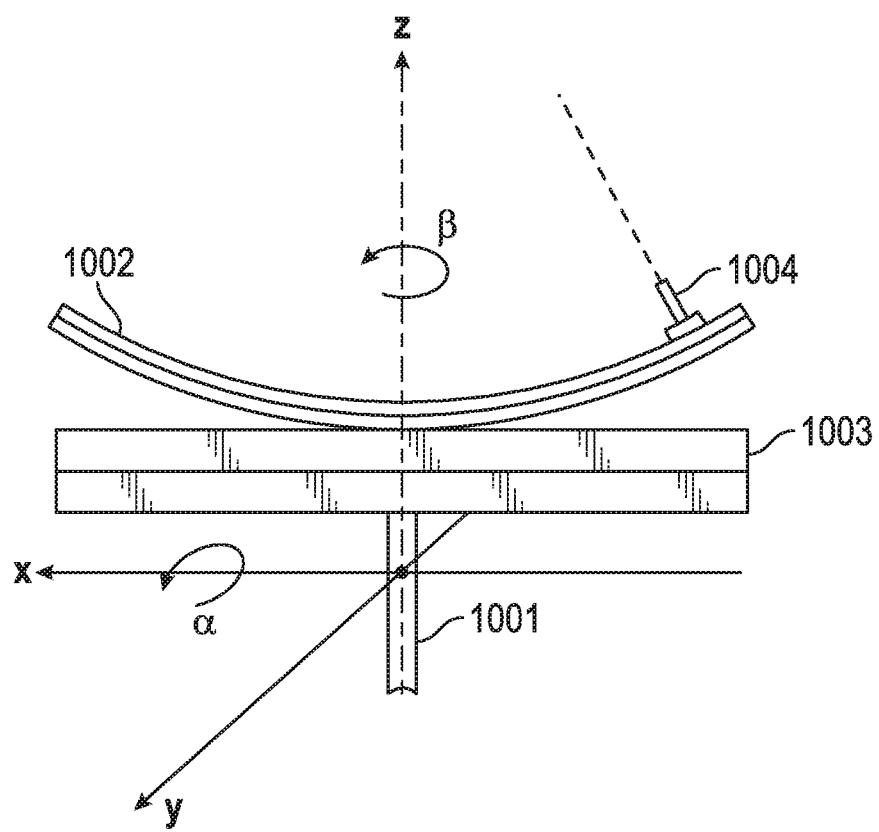
FIG. 10 illustrates the co-ordinate system used by the scanning devices of the present disclosure.

FIG. 10 illustrates the co-ordinate system used by the scanning devices of the present disclosure. As discussed in FIG. 1, the scanning device is comprised of a scan head positioning device of which only a portion 1001 is shown in FIG. 10 and a scan head further comprising a linear guide track 1003, an arcuate guide track 1002 and a transducer carriage 1004 on which an ultrasound transducer is mounted. The ultrasound beam emitted by the transducer is always aimed at the center of curvature of the arcuate guide track 1002.

The linear guide track 1003 can be held stationary while the transducer carriage 1004 moves back and forth along the arcuate guide track 1002 to form an arc scan. The linear guide track 1003 can move back and forth along the x-axis to form to a linear scan. Both the arcuate and linear guide tracks can be moved to form more complex scanning motions. This scan head configuration and its various scanning motions are described in detail in U.S. Pat. No. 8,317,709 which is incorporated herein by reference.

The positioner mechanism 1001 is also discussed in detail also in U.S. Pat. No. 8,317,709. The positioner mechanism can move the scan head in the x, y and z directions as well as rotate the scan head around the z-axis through an angle beta. These motions are typically used to position the scan head relative to the patient prior to scanning.

The positioner mechanism includes the ability to move the scan head in the y-direction which allows types of scans described in FIGS. 9A-9C.

As illustrated in FIG. 10, the positioner mechanism can also be modified to include a tilting mechanism centered at the origin of the x-y-x co-ordinate system to allow the scan head to be tilted or rotated about the x-axis thru an angle alpha. The ability to tilt the scan head allows types of scans described in FIGS. 9D-9F.

The z-axis is aligned with the axis of the positioner mechanism 1001. Positive motion along the z-axis moves the scan head towards the patient's prostate gland. The x and y directions are in a plane normal to the z-axis. The arcuate guide track 1002 is aligned with the x-axis such that the transducer carriage 1004 moves back and forth in the x-z plane along the arcuate guide track 1002. The motion of the linear guide track 1003 is back and forth along the x-axis. The beta direction represents rotation of the positioner mechanism and scan head around the z-axis. The angle alpha represents the tilt angle of the positioner mechanism and scan head. The tilt angle is changed by rotating the scan head about the x-axis.

Figure 11:
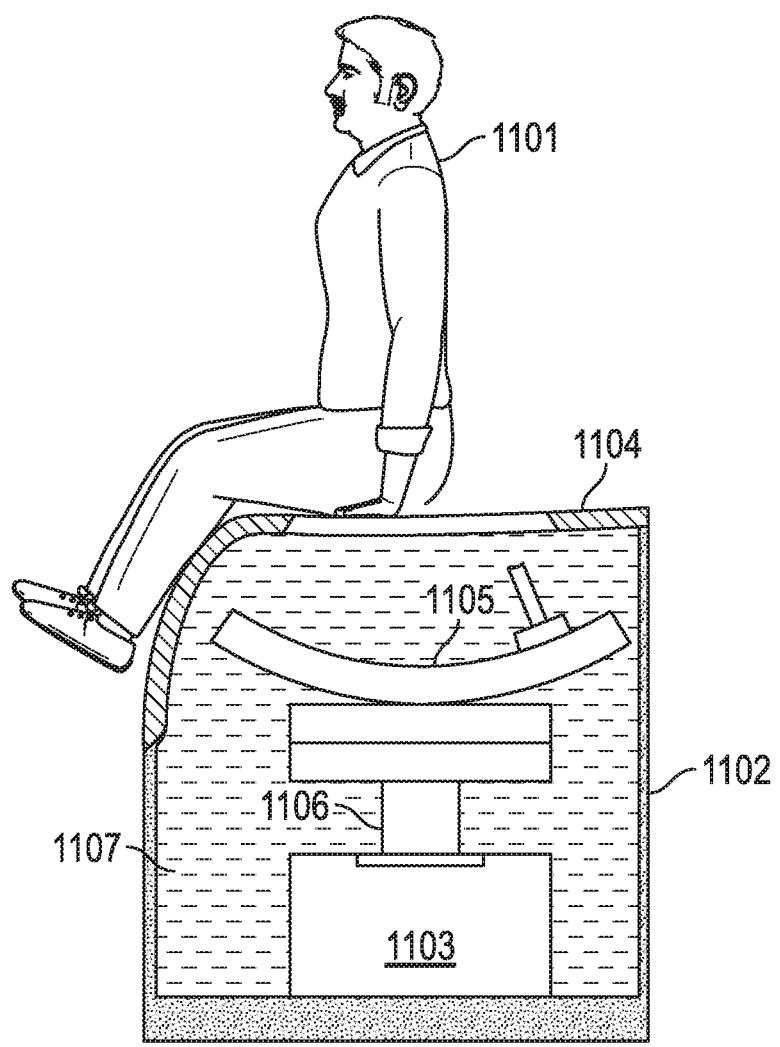
FIG. 11 is a schematic of a bowl seating apparatus with an ultrasound scanner inside and a patient in position for scanning the prostate.

FIG. 11 is a schematic of a bowl seating apparatus with an ultrasound scanner inside and a patient 1101 in position for scanning the prostate. In a scanning operation, the patient 1101 remains immobile on the top wall 1104 of the enclosure as shown, for example in the bowl apparatus of FIG. 11. Since the lower end of the positioning mechanism 1106 is fixed with respect to the support surface 1102, the lower end of the positioning mechanism 1106 is also fixed with respect to the patient 1101. Any prescribed movement of the top end of the positioning mechanism 1106 and any prescribed movement of the scan head 1105 is recorded by a magnetic or optical based positioning system such as described in U.S. Pat. No. 8,758,252 which is incorporated herein by reference.

An instrument volume 1103 is separate from the fluid (typically distilled water) in the interior volume 1107 of the enclosure. A computer and other equipment are contained in instrument volume 1103 while the scanning apparatus (top of the positioning mechanism and scan head) are contained in the interior volume 1107 of the enclosure.

The ability to precisely, accurately and reproducibly determine the location of the scan head at all times relative to the patient enables the system of the present disclosure to generate high resolution ultrasound images of a selected organ of a patient as long as the reflected ultrasound waveforms can be detected.

For imaging and treating a prostate, the imaging transducer and the irradiating transducer may be positioned with respect to the perineum by using the positioning mechanism of the arc scanning device or by a separate transducer holder positioning mechanism attached to the scan head. For example, in FIG. 1, a transducer carriage 104 can be designed to carry both the imaging transducer and the irradiating transducer. This would allow the transducers to be positioned for imaging or irradiating by using the positioner mechanism 109 of the arc scanning device. Alternately, this would allow the transducers to be positioned for imaging or irradiating by moving the transducer carriage 104 along the arcuate track 102 to a desired position.

An example of a separate transducer holder positioning mechanism attached to the scan head is illustrated in FIGS. 12A-12B which shows a schematic of a revolver type swept beam transducer holder positioning mechanism attached to the scan head. FIG. 12A shows a top view of the holder looking down at a 5 mm diameter imaging transducer and a 19 mm diameter HIFU transducer. FIG. 12B show a side view of the holder 1203, the 5 mm diameter imaging transducer 1202 and a 19 mm diameter HIFU transduce 1203. When one of the transducers is properly positioned with respect to the target of interest, then the other transducer can be rotated into this position as needed. In other words, either transducer can be positioned to be properly located and aligned to irradiate or image the target of interest. As can be appreciated, the diameter of imaging transducers are typically in the range of about 5 mm to about 17 mm and the diameter of irradiating transducers are typically in the range of about 20 mm to about 60 mm.

Modes of Operation

In a first mode, an imaging transducer and an irradiating therapeutic transducer are mounted in a revolver type holder such as shown in FIGS. 12A-12B. The imaging transducer may be rotated into position with respect to the prostate and an image made of the prostate scanning up through the perineum. Then the irradiating transducer may be rotated into position with respect to the prostate and the prostate can also be irradiated up through the perineum. Then the imaging transducer may be rotated back into position and an image made of the irradiated prostate.

The irradiating transducer required for this task is typically in the range of about 17 mm diameter to about 30 mm in diameter, typically in the frequency range of about 5 MHz to about 20 MHz and typically has a focal length in the range of about 20 mm to about 40 mm. The imaging transducer is typically in the range of about 4 mm diameter to about 7 mm in diameter, typically in the frequency range of about 25 MHz to about 40 MHz and typically has a focal length in the range of about 20 mm to about 40 mm. The irradiating transducer would likely require its own pulser/receiver board while the imaging transducer, which requires much less power, would have a separate pulser/receiver board.

In a second mode, a single irradiating therapeutic transducer is used in a conventional holder. The irradiating transducer required is typically in the range of about 17 mm diameter to about 30 mm in diameter, typically in the frequency range of about 5 MHz to about 20 MHz and typically has a focal length in the range of about 20 mm to about 40 mm.

When operating in this second mode, coded excitation and tissue harmonic imaging techniques may be used to image the irradiated tissue. For example, a 15 MHz irradiating transducer would produce a strong second harmonic at about 30 MHz that could be used for imaging. As noted previously, tissue harmonic ultrasound imaging has been used in medical ultrasound imaging since the 1990s.

As can be appreciated, the first mode of operation can be extended to include coded excitation and tissue harmonic imaging techniques to produce images at different frequencies and/or with different focal length transducers. For example, an imaging transducer and an irradiating therapeutic transducer can be mounted in a revolver type holder. The irradiating transducer could be about a 12 MHz transducer with a focal length of about 20 mm to about 40 mm that would produce a strong second harmonic at about 24 MHz that could be used for imaging. The imaging transducer with a focal length of about 10 mm to about 20 mm typically operates in the range of about 25 MHz to about 40 MHz.

This combination cited in the above example could be used to irradiate the target organ with non ionizing ultrasound while taking images of the target organ at 12 MHz, 24 MHz, and 40 MHz.

A number of variations and modifications of the disclosed subject matter can be used. As will be appreciated, it would be possible to provide for some features of the disclosure without providing others.

The present disclosure, in various embodiments, includes components, methods, processes, systems and/or apparatus substantially as depicted and described herein, including various embodiments, sub-combinations, and subsets thereof. Those of skill in the art will understand how to make and use the present disclosure after understanding the present disclosure. The present disclosure, in various embodiments, includes providing devices and processes in the absence of items not depicted and/or described herein or in various embodiments hereof, including in the absence of such items as may have been used in previous devices or processes, for example for improving performance, achieving ease and\or reducing cost of implementation.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the disclosure.

Moreover, though the description of the disclosure has included description of one or more embodiments and certain variations and modifications, other variations and modifications are within the scope of the disclosure, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed:

1. A system for treating and imaging a body part of a patient, comprising:
    a housing defining an enclosed volume, wherein the enclosed volume is at least partially filled with a fluid;
    a transducer holder positioned in the fluid in the enclosed volume of the housing, wherein the transducer holder is movable among a plurality of positions;
    a first ultrasound transducer positioned on the transducer holder, wherein the first ultrasound transducer emits a first ultrasound wave in a first frequency range;
    a second ultrasound transducer positioned on the transducer holder, wherein the second ultrasound transducer emits a second ultrasound wave in a second frequency range,
    wherein the first and second frequency ranges are distinct,
    wherein the transducer holder moves such that one of the first or second ultrasound transducers is in a position of the plurality of positions and an orientation to emit one of the first or second ultrasound waves, respectively, for forming an image of a body part of a patient; and
    wherein the transducer holder moves such that another one of the first or second ultrasound transducers is in the position of the plurality of positions and the orientation to transmit another one of the first or second ultrasound waves, respectively, to treat the body part of a patient.

2. The system of claim 1, further comprising:
    an acoustically-transparent window on a surface of the housing, wherein one of the first or second ultrasound transducer emits one of the first or second ultrasound waves, respectively, through the acoustically-transparent window and into the body part of the patient.

3. The system of claim 1, wherein the first frequency range is between approximately 5 MHz and 20 MHz, and the second frequency range is between approximately 25 MHz and 40 MHz.

4. The system of claim 1, wherein a focal length of the first ultrasound transducer is between approximately 20 mm and 40 mm, and a focal length of the second ultrasound transducer is between approximately 12 mm and 40 mm; wherein the focal length of the first ultrasound transducer is distinct from the focal length of the second ultrasound transducer.

5. The system of claim 1, wherein, when the first ultrasound transducer is in an emission position, the first ultrasound transducer emits the first ultrasound wave at a first frequency in the first frequency range, and the first ultrasound transducer receives both the first ultrasound wave at the first frequency and a harmonic wave at a harmonic frequency that is approximately twice the frequency of the first frequency.

6. The system of claim 5, wherein, when the second ultrasound transducer is in the emission position, the second ultrasound transducer emits the second ultrasound wave at a second frequency in the second frequency range, and the second frequency is greater than both the first and harmonic frequencies.

7. The system of claim 1, wherein the transducer holder is rotatable about an axis and has a surface that is orientated substantially perpendicular to the axis, wherein the first and second ultrasound transducers are positioned on the surface of the transducer holder, and wherein the transducer holder rotates such that one of the first or second ultrasound transducers is in an emission position.

8. The system of claim 1, further comprising:
    an arcuate track, wherein the transducer holder moves along the arcuate track such that one of the first or second ultrasound transducers is in an emission position.

9. The system of claim 1, wherein forming the image of the body part is enhanced by using at least one of tissue harmonic imaging and coded excitation techniques.

10. A method for treating and imaging a body part of a patient, comprising:
    providing a housing with an acoustically-transparent window on a surface of the housing, wherein the housing is at least partially filled with a fluid;
    providing a first ultrasound transducer and a second ultrasound transducer in the fluid in the housing, wherein the first ultrasound transducer emits a first ultrasound wave in a first frequency range, the second ultrasound transducer emits a second ultrasound wave in a second frequency range, and the first and second frequency ranges are distinct;
    positioning a patient on the housing with a body part positioned over the acoustically-transparent window;
    emitting the first ultrasound wave from the first ultrasound transducer, at a position and an orientation to image the body part of the patient;
    emitting the second ultrasound wave from the second ultrasound transducer at a same position and a same orientation as used in emitting the first ultrasound wave to treat the body part of the patient; and
    emitting the first ultrasound wave from the first ultrasound transducer to re-image the body part of the patient.

11. The method of claim 10, wherein treating the body part of the patient comprises at least one of heating or moving the body part of the patient.

12. The method of claim 10, further comprising:
    providing the first and second ultrasound transducers on a transducer holder that rotates about an axis, wherein the transducer holder rotates such that one of the first or second ultrasound transducers is in an emission position to emit one of the first or second ultrasound waves, respectively, through the acoustically-transparent window and into the body part of the patient.

13. The method of claim 12, further comprising:
    rotating the transducer holder such that the second ultrasound transducer is in the emission position to emit the second ultrasound wave and treat the body part of the patient; and
    rotating the transducer holder such that the first ultrasound transducer is in the emission position to emit the first ultrasound wave and re-image the body part of the patient.

14. The method of claim 10, further comprising:
    providing the first and second ultrasound transducers on a transducer holder that moves along an arcuate track;
    moving the transducer holder to a position on the arcuate track where the first ultrasound transducer is in an emission position to emit one of the first ultrasound wave through the acoustically-transparent window and into the body part of the patient; and moving the transducer holder to the position on the arcuate track where the second ultrasound transducer is in the emission position to emit one of the first ultrasound wave through the acoustically-transparent window and into the body part of the patient.

15. A system for treating and imaging a body part of a patient, comprising:
- a housing defining an enclosed volume, wherein the enclosed volume is at least partially filled with a fluid;
- an acoustically-transparent window on a surface of the housing;
- a transducer holder positioned in the fluid in the enclosed volume of the housing;
- a first ultrasound transducer positioned on the transducer holder, wherein the first ultrasound transducer emits a first ultrasound wave at a first frequency in a first frequency range at a common position and a common orientation through the acoustically-transparent window and into a body part of a patient to image the body part, and the first ultrasound transducer receives a harmonic wave at a harmonic frequency that is approximately twice the frequency of the first frequency; and
- a second ultrasound transducer position on the transducer holder, wherein the second ultrasound transducer emits a second ultrasound wave at a second frequency in a second frequency range at the common position and the common orientation through the acoustically-transparent window and into the body part of the patient to treat the body part, and wherein the first and second frequency ranges are distinct, and the second frequency is greater than both the first and harmonic frequencies.

16. The system of claim 15, wherein the transducer holder rotates such that one of the first or second ultrasound transducers is in an emission position to emit one of the first or second ultrasound waves, respectively, into a body part of a patient.

17. The system of claim 15, wherein a focal length of the first ultrasound transducer is between approximately 20 mm and 40 mm, and a focal length of the second ultrasound transducer is between approximately 12 mm and 40 mm; wherein the focal length of the first ultrasound transducer is distinct from the focal length of the second ultrasound transducer.

18. The system of claim 15, further comprising: an arcuate track, wherein the transducer holder moves along the arcuate track such that one of the first or second ultrasound transducers is in an emission position to emit one of the first or second ultrasound waves, respectively, into a body part of a patient.

19. The system of claim 18, further comprising:
- a linear track, wherein the arcuate track moves along a longitudinal length of the linear track.

20. The system of claim 19, further comprising:
- a positioning mechanism interconnected to the linear track, wherein the positioning mechanism moves the linear track in at least a first horizontal direction, a second horizontal direction, and a vertical direction.

* * * * *